(12) United States Patent
Zhang et al.

(10) Patent No.: US 9,029,566 B2
(45) Date of Patent: May 12, 2015

(54) ROSIN DERIVED EPOXIDES AND CURING AGENTS

(75) Inventors: Jinwen Zhang, Pullman, WA (US); Xiaoqing Liu, Pullman, WA (US); Ming Xian, Pullman, WA (US)

(73) Assignee: Washington State University, Pullman, WA (US)

( * ) Notice: Subject to any disclaimer, the term of this patent is extended or adjusted under 35 U.S.C. 154(b) by 1093 days.

(21) Appl. No.: 13/119,146

(22) PCT Filed: Sep. 16, 2009

(86) PCT No.: PCT/US2009/057157
§ 371 (c)(1), (2), (4) Date: Mar. 15, 2011

(87) PCT Pub. No.: WO2010/033593
PCT Pub. Date: Mar. 25, 2010

(65) Prior Publication Data
US 2011/0172440 A1 Jul. 14, 2011

Related U.S. Application Data

(60) Provisional application No. 61/192,324, filed on Sep. 16, 2008.

(51) Int. Cl.
*C07D 405/14* (2006.01)
*C07D 407/12* (2006.01)
*C07D 407/14* (2006.01)
*C07D 209/02* (2006.01)
*C07D 303/17* (2006.01)

(52) U.S. Cl.
CPC .......... *C07D 407/12* (2013.01); *C07D 209/02* (2013.01); *C07D 303/17* (2013.01); *C07D 405/14* (2013.01); *C07D 407/14* (2013.01)

(58) Field of Classification Search
None
See application file for complete search history.

(56) References Cited

U.S. PATENT DOCUMENTS 5,116,945 A 5/1992 Osawa et al.

OTHER PUBLICATIONS

Plasticheskie Massy, 6:11 (1977) (Abstract only).*
Ikeda, et al., JOACS, 66:822 (1989).*
Atta et al., "Synthesis and Characterization of Tetra-Functional Epoxy Resins from Rosin," *Journal of Polymer Research* 12:127-138, 2005.
Wang et al., "Synthesis of rosin-based flexible anhydride-type curing agents and properties of the cured epoxy," *Polym Int* 58:1435-1441, 2009. (Published online Sep. 2, 2009).
International Search Report from corresponding PCT Application No. PCT/US2009/057157 dated Apr. 29, 2010.
Written Opinion of the International Search Report from corresponding PCT Application No. PCT/US2009/057157 dated Apr. 29, 2010.

* cited by examiner

*Primary Examiner* — Michael Barker
(74) *Attorney, Agent, or Firm* — Klarquist Sparkman, LLP

(57) ABSTRACT

An epoxide agent for an epoxy resin system, the epoxide agent comprising at least one non-acid functional rosin moiety and at least one epoxide moiety. Another embodiment is a curing agent for an epoxy resin system comprising at least one non-acid functional rosin moiety and at least one moiety that is reactive with an epoxy.

1 Claim, 10 Drawing Sheets

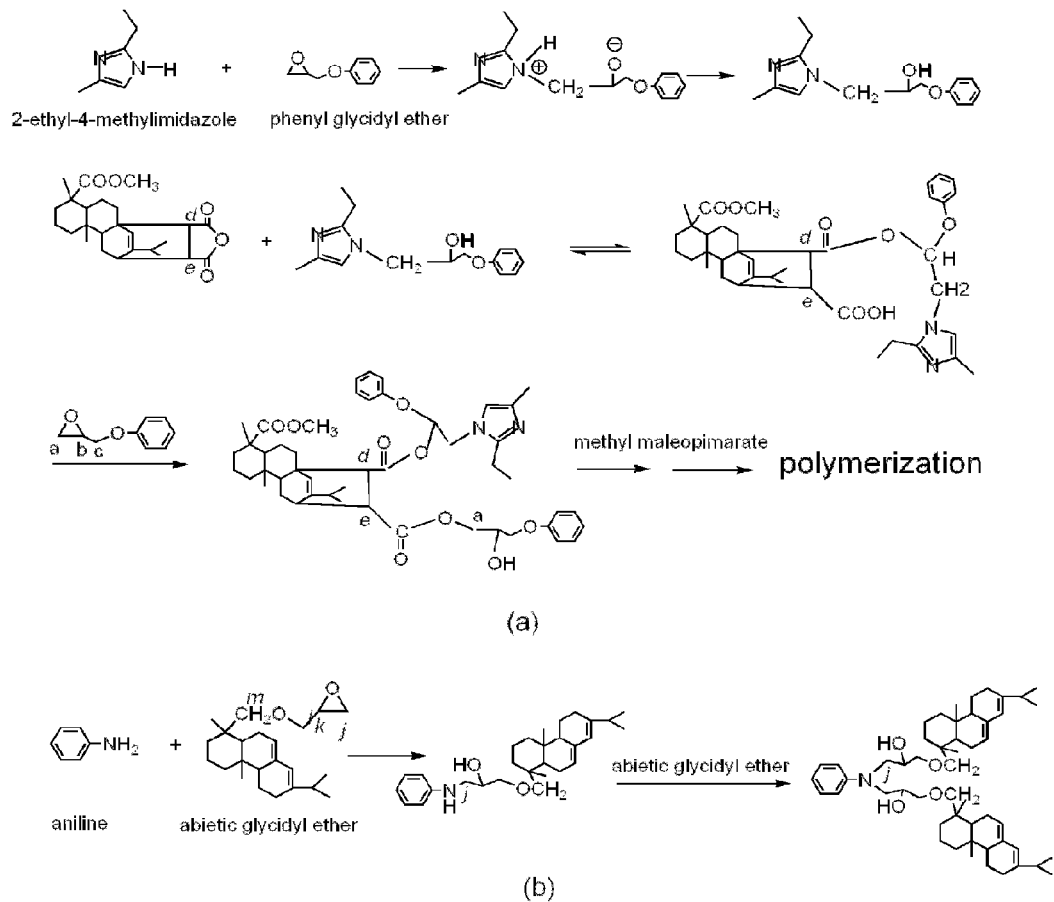
FIG. 1. Curing reactions of methyl maleopimarate/phenyl glycidyl ether (a), and abietyl glycidyl ether/aniline (b).

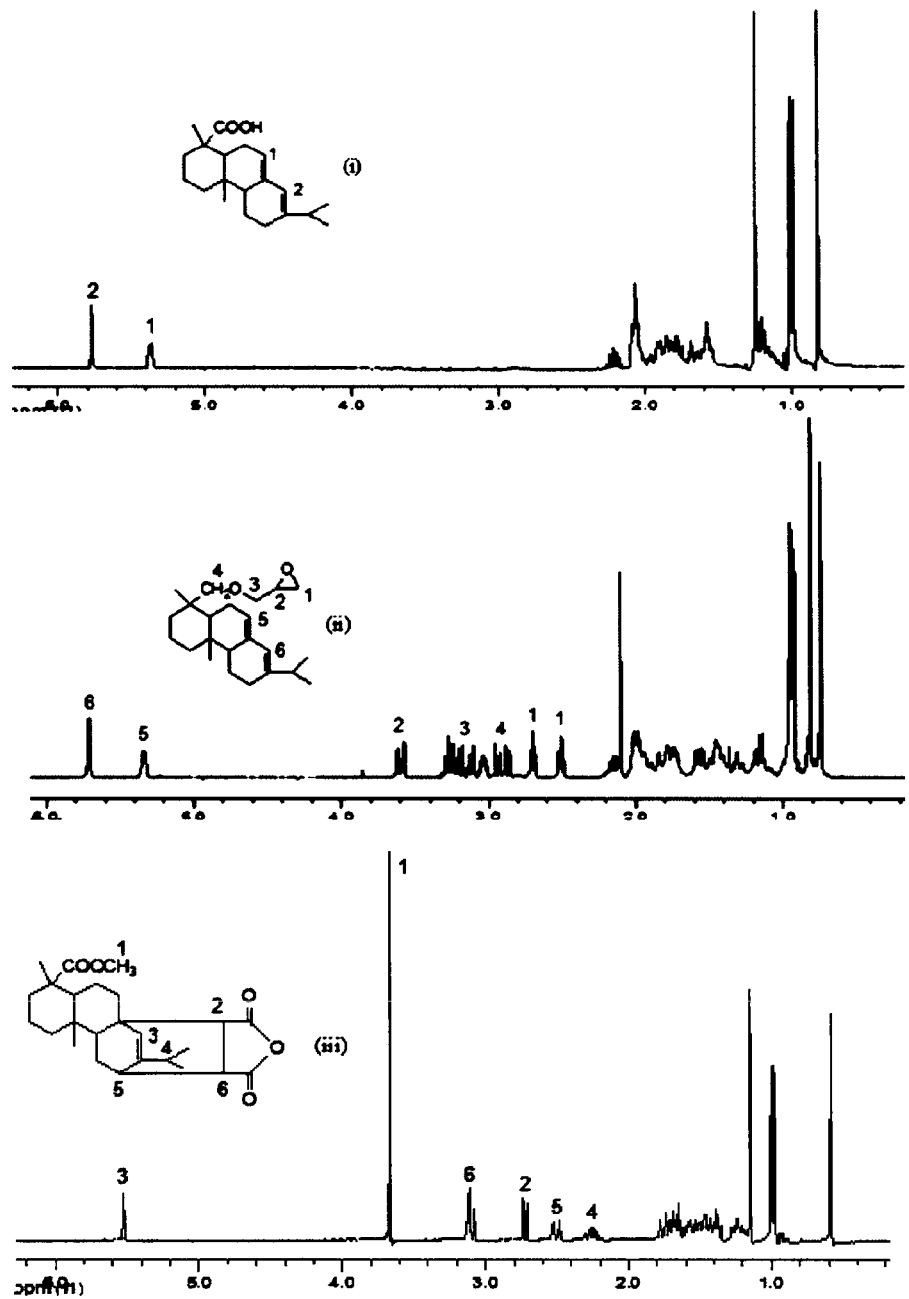
FIG. 2. $^1$H NMR spectra of (i) abietic acid (ii) abietyl glycidyl ether (iii) methyl maleopimarate

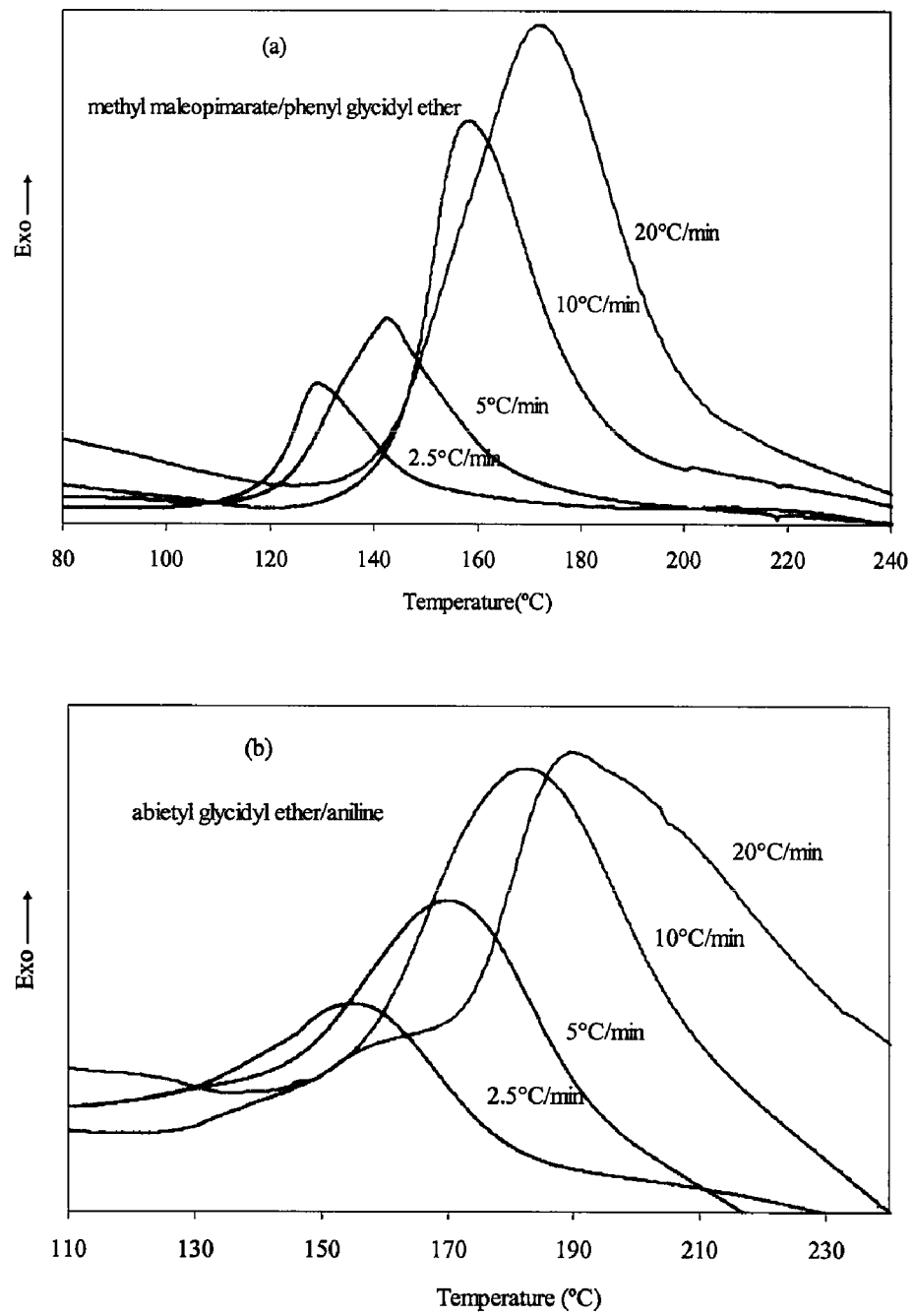
FIG. 3. DSC thermograms of curing of model compounds at different heating rates

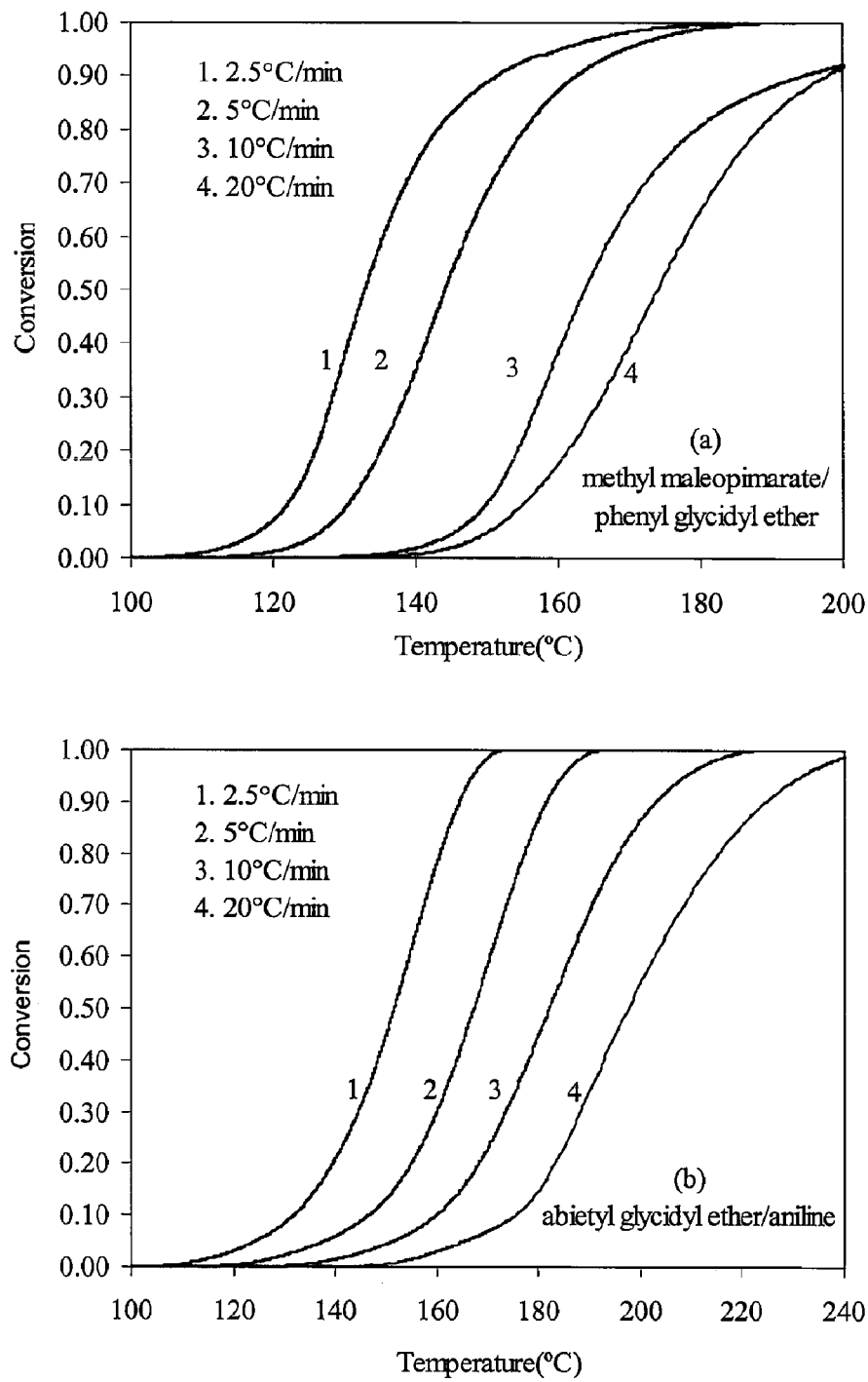
FIG. 4. Degree of conversion versus temperature at different heating rates

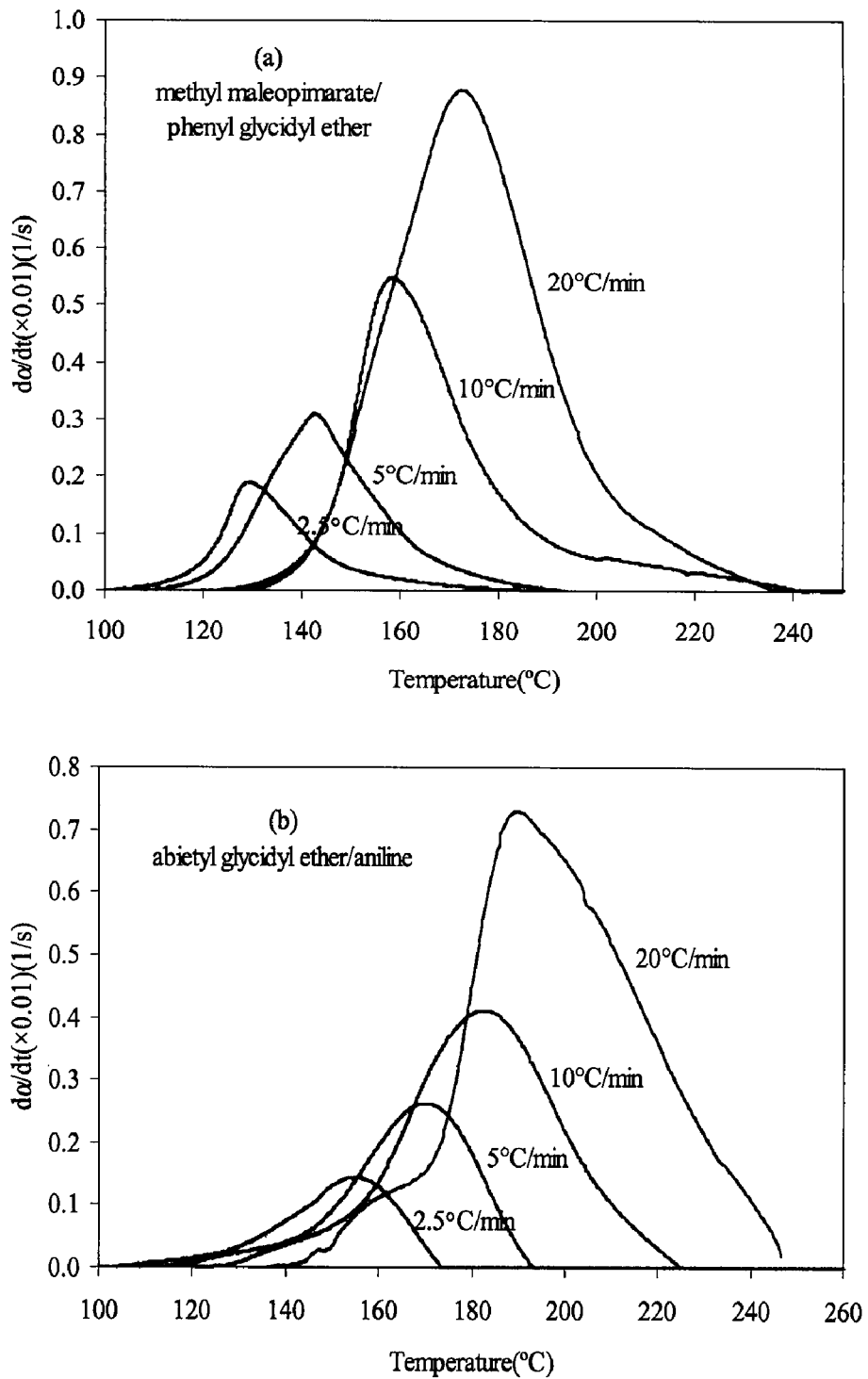
FIG. 5. Effect of heating rate on reaction rate

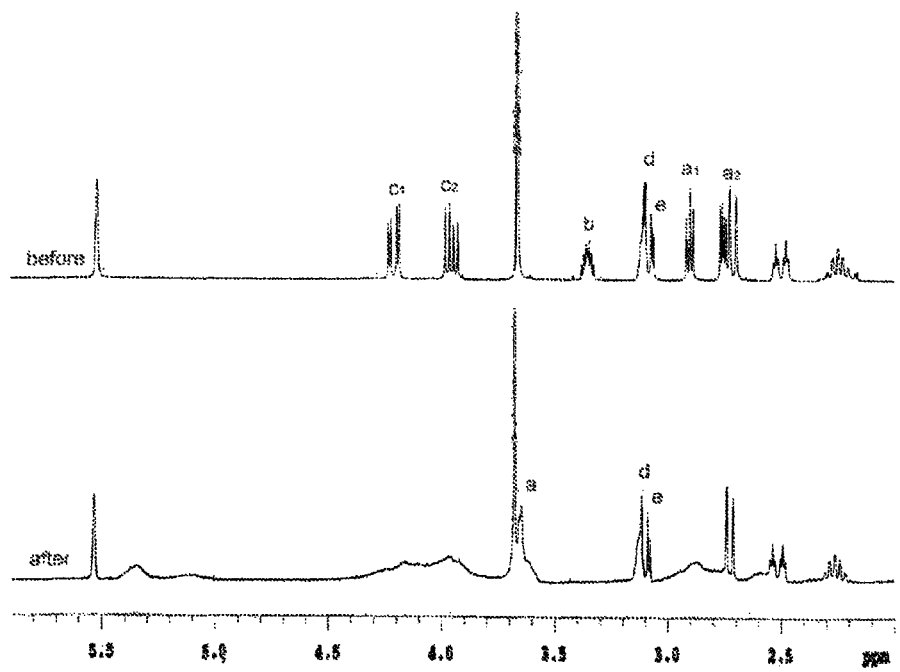
FIG. 6(a). Methyl maleopimarate/1,2-epoxy-3-phenoxy propane
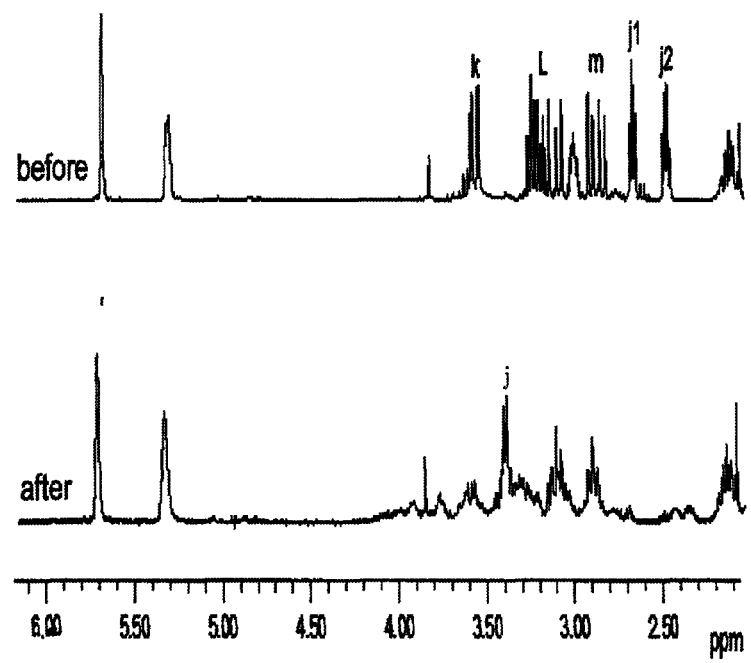
(b) Abietyl glycidyl ether/aniline
FIG. 6(b). $^1$H NMR spectra before and after curing reaction Table 1. DSC results of nonisothermal curing of the methyl maleopimarate/phenyl glycidyl ether system

| $\beta$ (K/min) | $\Delta H$ (J/g) | $\Delta H$ (KJ/mol)[1] | $T_i$ (K) | $T_p$ (K) | $T_e$ (K) |
|---|---|---|---|---|---|
| 20 | 112.4 | 80.4 | 411.8 | 444.2 | 499.5 |
| 10 | 151.8 | 108.5 | 406.7 | 430.8 | 505.8 |
| 5 | 128.4 | 91.8 | 390.1 | 415.3 | 457.8 |
| 2.5 | 139.6 | 99.8 | 380.9 | 402.1 | 451.4 |
| 0[2] | 127.9[3] | 91.5[3] | 392 | 402 | 422 |

1. On the basis of per mole of epoxide.
2. Linear extrapolation at $dT/dt = 0$.
3. Extrapolated enthalpy was made by excluding the result at heat rate of 20°C/min.

FIG. 7

Table 2. DSC results of nonisothermal curing of the abietyl glycidyl ether/aniline system

| $\beta$ (K/min) | $\Delta H$ (J/g) | $\Delta H$ (KJ/mol)[1] | $T_i$ (K) | $T_p$ (K) | $T_e$ (K) |
|---|---|---|---|---|---|
| 20 | 55.4 | 21.6 | 423.0 | 463.2 | 516.6 |
| 10 | 105.5 | 41.2 | 408.7 | 455.1 | 491.8 |
| 5 | 93.5 | 36.5 | 394.5 | 443.9 | 463.5 |
| 2.5 | 90.3 | 35.3 | 382.7 | 429.2 | 444.6 |
| 0[2] | 84.3[3] | 33.0[3] | 397 | 431 | 448 |

1. On the basis of per mole of epoxide.
2. Linear extrapolation at $dT/dt = 0$.
3. Extrapolated enthalpy was made by excluding the result at heat rate of 20°C/min.

FIG. 8

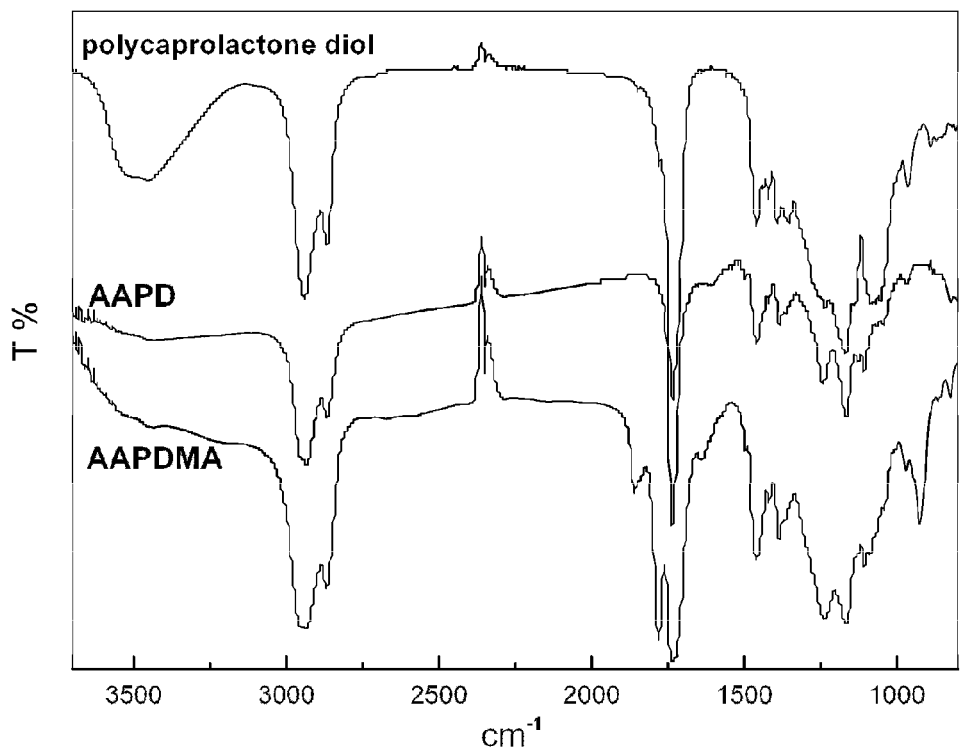
FIG. 9. FT-IR spectra for polycaprolactone diol, AAPD and AAPDMA
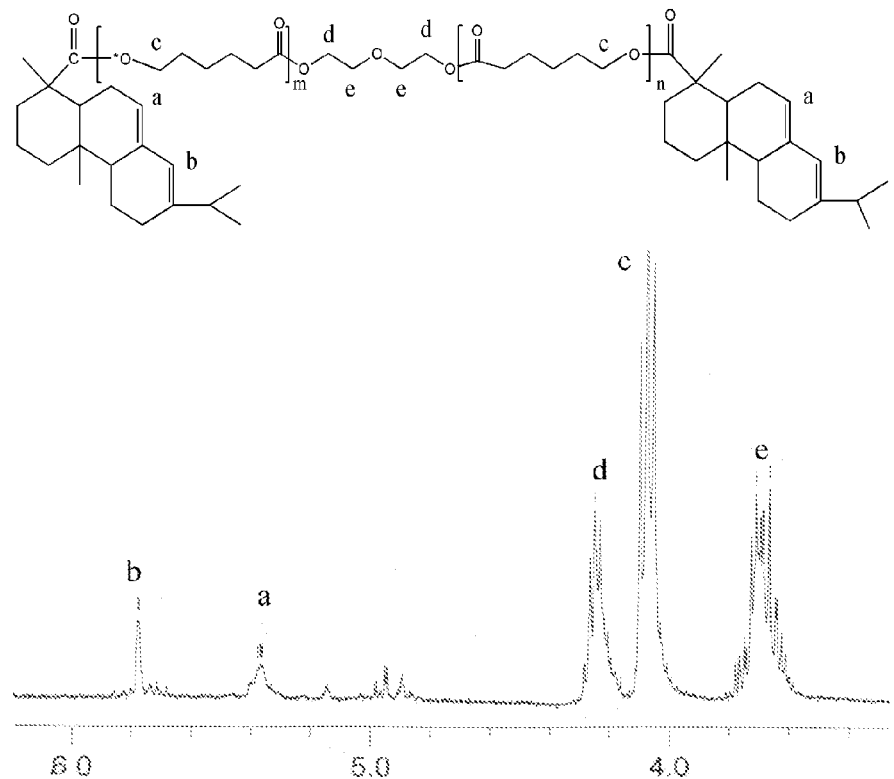
FIG. 10. The $^1$H-NMR spectra for AAPD

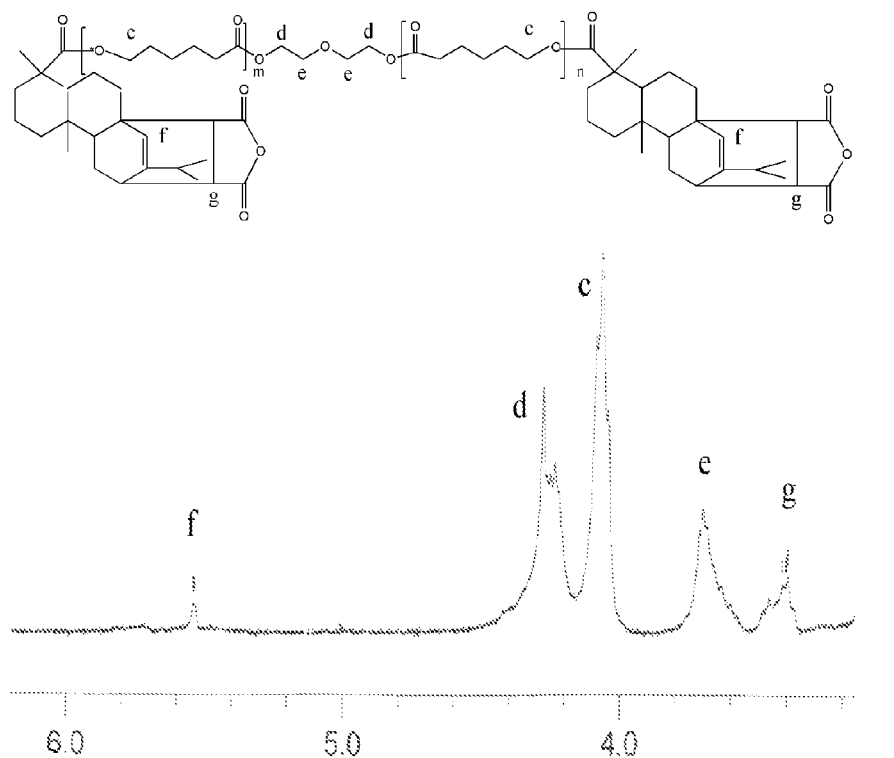
FIG. 11. The $^1$H-NMR spectra for AAPDMA
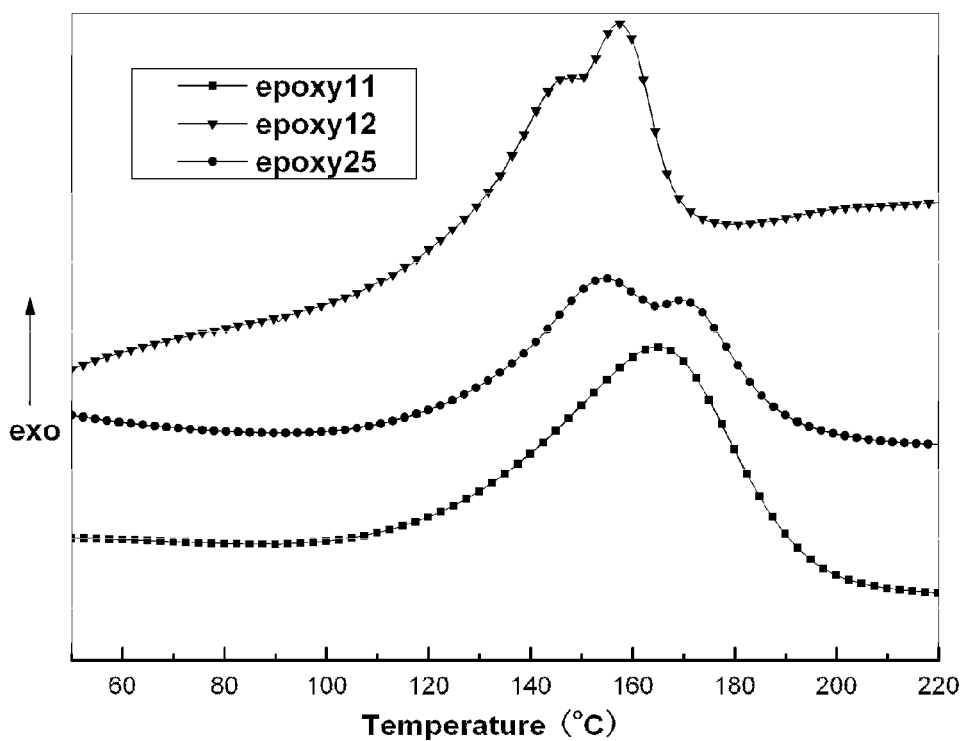
FIG. 12. The DSC diagram of epoxy 11, epoxy12 and epoxy25

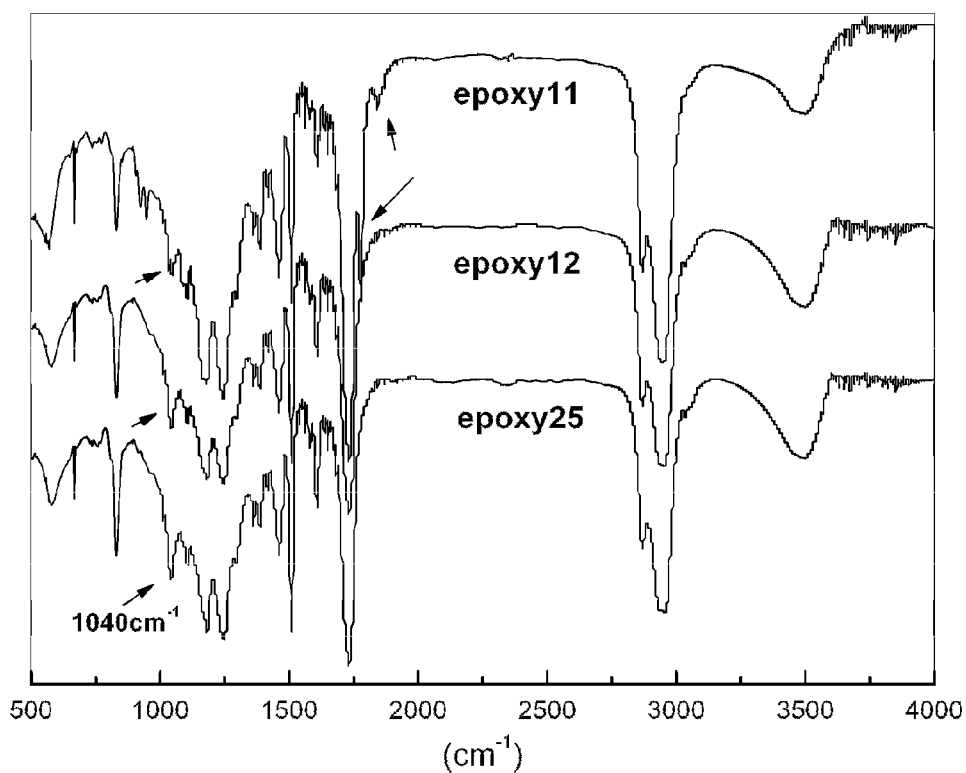
FIG. 13. FT-IR spectra of different epoxy system
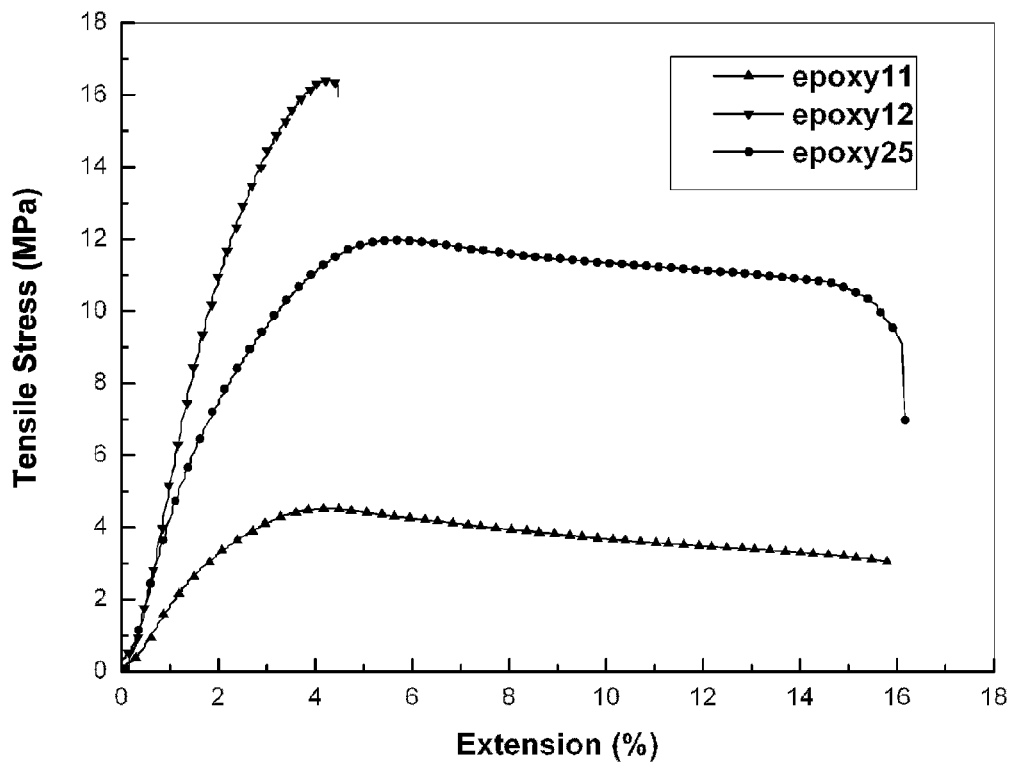
FIG. 14. The tensile properties of different epoxy system

ROSIN DERIVED EPOXIDES AND CURING AGENTS

CROSS REFERENCE TO RELATED APPLICATION APPLICATIONS

This is the U.S. National Stage of International Application No. PCT/US2009/057157, filed Sep. 16, 2009, which was published in English under PCT Article 21(2), which in turn claims the benefit of, and priority to, U.S. Provisional Patent Application No. 61/192,324 filed on Sep. 16, 2008, both of which are incorporated herein in their entirety.

FIELD

This disclosure relates to epoxides and curing agents that are synthesized from rosin.

BACKGROUND

Rosin is an abundantly available natural product. Rosin is mainly obtained from the exudation of pines and conifers. It is also obtained by the distillation of crude tall oil, which is a byproduct in the Kraft pulp process, or from aged pine stumps. Total world production of rosin is approximately 1.2 million tons annually. Rosin is a mixture of acidic (ca. 90%) and neutral (ca. 10%) compounds. The acidic components, generally named rosin (or resin) acids, are also a mixture containing mainly isomeric abietic-type acids (40-60%) and pimaric-type (9-27%) acids on the basis of total rosin weight. The exact composition of rosin acids varies, depending on the tree species and production location. Rosin and its derivatives have long been used as adhesive tackifiers, and are still mainly used in that market. In addition, rosin and its derivatives have also found other niche applications in printing inks, varnishes, paints, sealing wax, some soaps, paper sizing; soldering, plasters, etc.

In recent years, the drive for obtaining chemicals and materials from renewable resources has also prompted the research of new applications for rosin. Rosin acids, owing to their characteristic fused ring structure, are analogous to many aromatic compounds in rigidity. Therefore, rosin and its derivatives could become important alternatives to current fossil carbon-based aromatic monomer compounds in polymers.

In addition, epoxy adhesives are widely used in the aerospace, automatic, electronic and construction industries because of their outstanding mechanical properties, better wetting ability, good chemical and solvent resistance. However, the common epoxy resin are always rigid and brittle, which weakens their peeling properties and impact strength, and then limits their application field. To minimize the major shortcoming of this kind of adhesive, a number of techniques, such as flexibilizing the chemical structure of epoxy or incorporating modifiers into the adhesives, have been used.

SUMMARY

According to first embodiment, there is disclosed herein an epoxide agent for an epoxy resin system, the epoxide agent comprising at least one non-acid functional rosin moiety and at least one epoxide moiety.

In another embodiment, there is disclosed herein a curing agent for an epoxy resin system comprising at least one non-acid functional rosin moiety and at least one moiety that is reactive with an epoxy.

In a further embodiment, there is disclosed herein a curing agent for an epoxy resin system, the curing agent comprising a modified rosin comprising a reaction product of a non-acid functional rosin with at least one functionalizing molecule.

Also disclosed herein in an additional embodiment is an epoxide agent for an epoxy resin system, the epoxide agent comprising a modified rosin comprising a reaction product of a non-acid functional rosin with at least one functionalizing molecule, wherein the epoxide agent includes at one epoxide moiety.

Another embodiment disclosed herein is a curing agent for an epoxy resin system, the curing agent comprising the reaction product of:
  reacting a rosin acid with at least one first functionalizing molecule to obtain a modified rosin acid; and
  reacting the modified rosin acid with at least one second functionalizing molecule to obtain a non-acid functional rosin reaction product.

A further disclosed embodiment is an epoxide agent comprising the reaction product of:
  reacting a rosin acid with at least one first functionalizing molecule to obtain a modified rosin acid; and
  reacting the modified rosin acid with at least one second functionalizing molecule to obtain a non-acid functional rosin reaction product.

An additional disclosed embodiment is a curing agent for an epoxy resin system, the curing agent comprising at least two modified rosin acid moieties covalently bridged together with a bridge moiety R, wherein the curing agent is a reaction product of rosin acid and a Diels-Alder reagent.

Also disclosed herein are epoxy resins produced from any of the above-described curing agents or epoxide agents, and powder coating compositions comprising the above-described curing agents or epoxide agents.

Also disclosed herein are compounds comprising a structure represented by at least one of the following formulae:

Structure 1

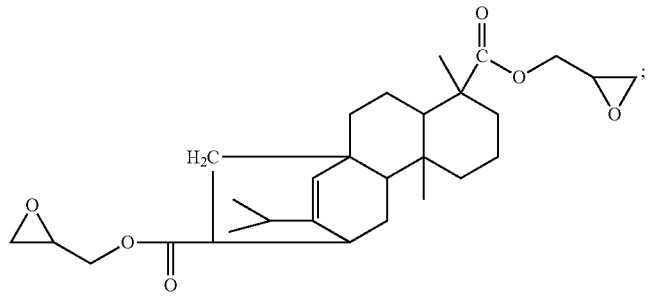

-continued
Structure 2
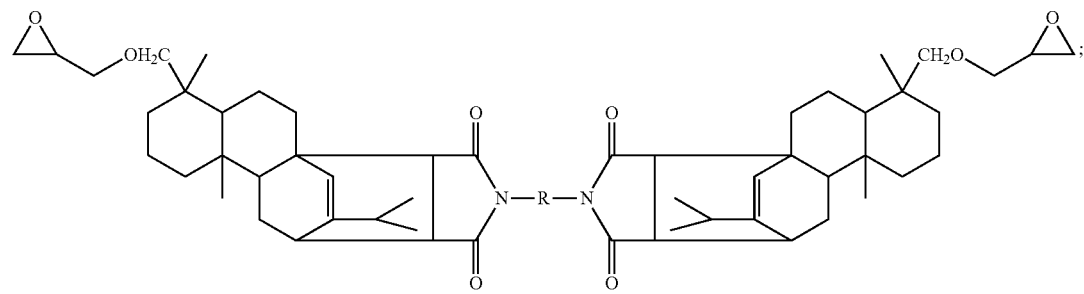
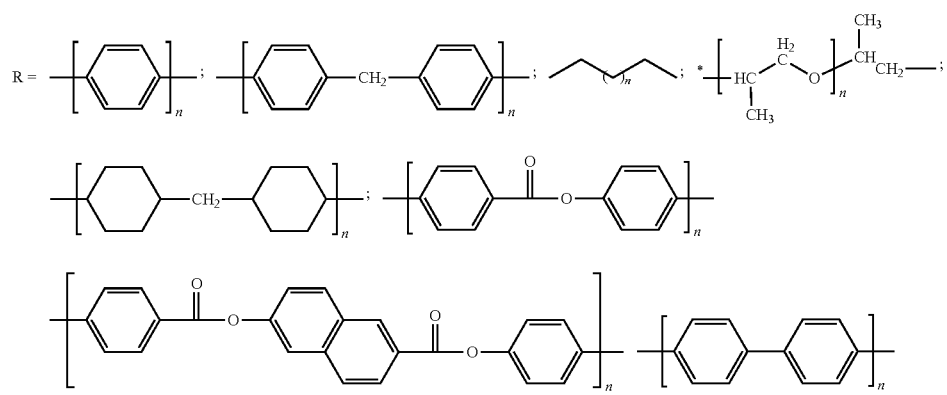
(n = 1-10)
Structure 3
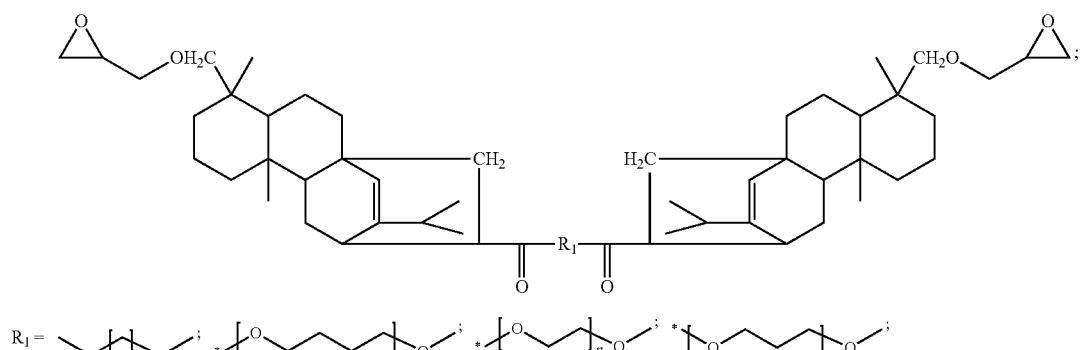
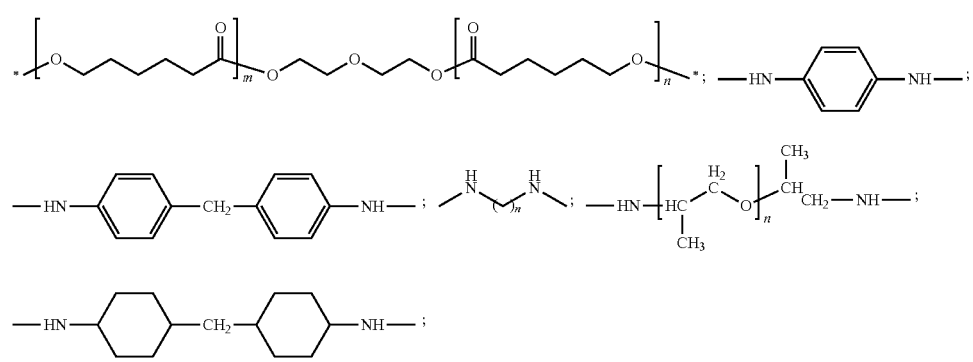
(n = 1-10)
(m = 1-10)

-continued
Structure 5
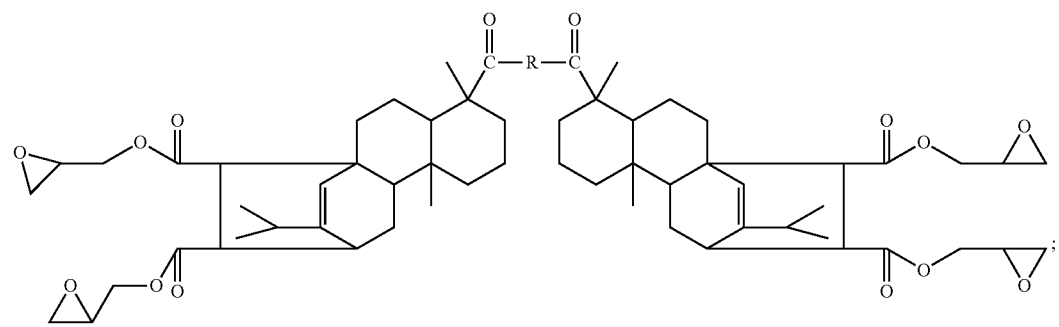
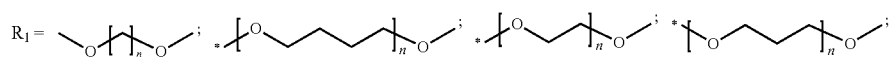
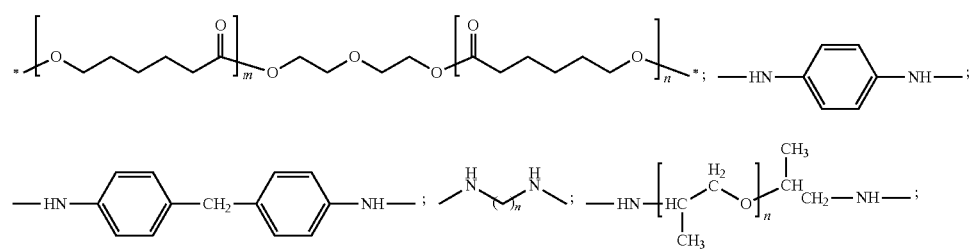
(n = 1-10)
(m = 1-10)
Structure 10
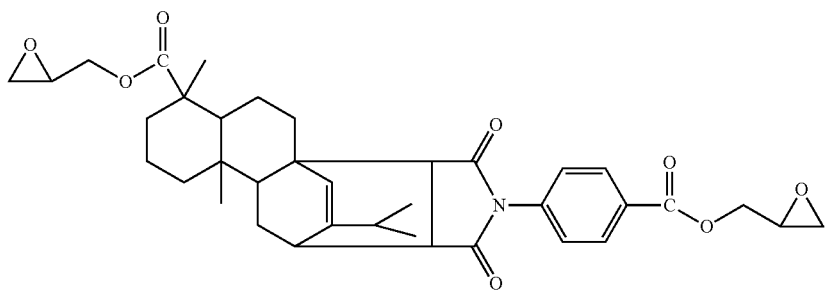
Structure 11
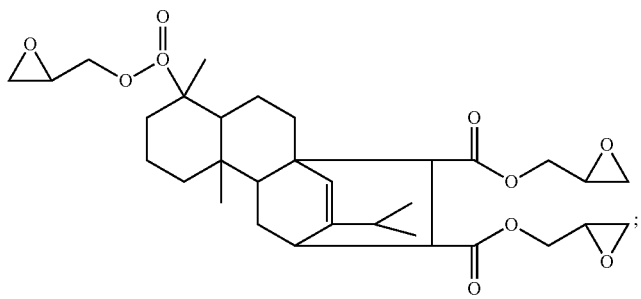

Structure 4
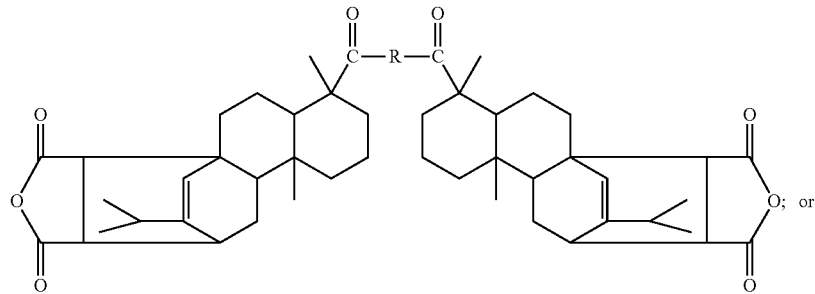
; or
R = 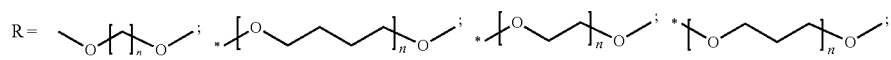
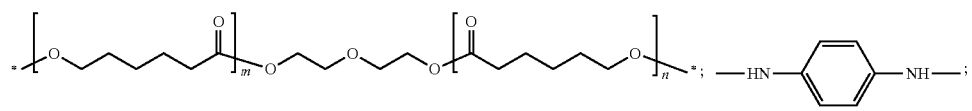
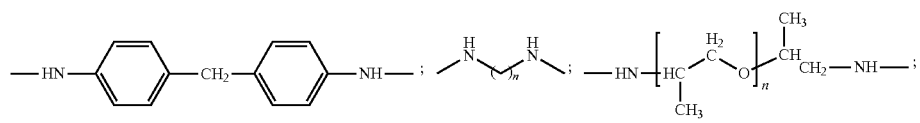
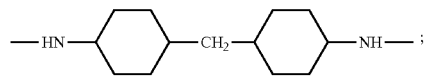
(n = 1-10)
(m = 1-10)
Structure 7
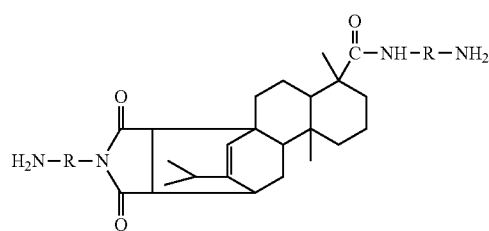
Structure 6
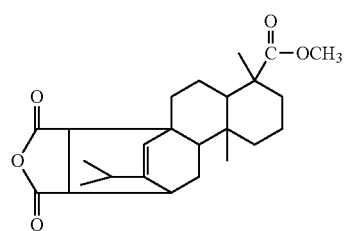
Structure 8
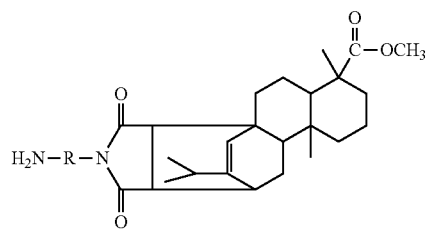
Structure 9
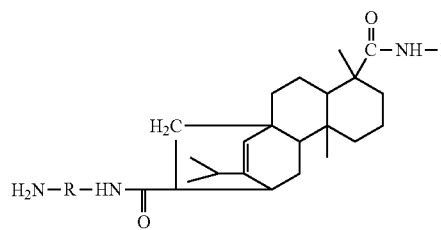

-continued

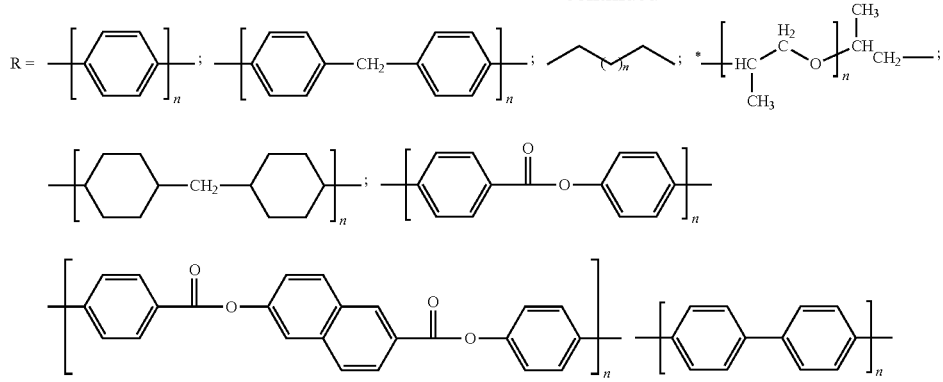

(n = 1-10)

According to another embodiment, there is disclosed herein a non-acid functional modified rosin compound comprising at least one rosin acid moiety that has been modified with at least one modifying functional group selected from glycidyl ether, glycidyl ester, anhydride, carboxylic acid, amine, polyamine, or a mixture thereof.

Also disclosed herein are methods for making a rosin-derived epoxy, comprising:

reducing at least one carboxyl group of at least one rosin acid moiety to a hydroxyl group to produce an intermediate; and reacting the hydroxyl group of the intermediate with an epoxide to produce a rosin-derived epoxy.

Additionally disclosed methods are methods for making a rosin-derived curing agent, comprising:

reacting at least one carboxyl group of at least one first rosin acid moiety with a first functional moiety-containing reactant; and reacting at least one diene group of at least one second rosin acid moiety with a second functional moiety-containing reactant, wherein at least one of the first functional moiety or the second functional moiety is selected from anhydride, carboxylic acid, amine or polyamine.

A further disclosed method for making a compound comprises:

reacting a non-acid functional rosin with at least one functionalizing molecule, wherein the functionalizing molecule includes at least one functional group selected from glycidyl ether, glycidyl ester, anhydride, carboxylic acid, amine, or polyamine.

Another disclosed method for making a compound comprises:

reacting a rosin acid with at least one first functionalizing molecule to obtain a modified rosin acid; and reacting the modified rosin acid with at least one second functionalizing molecule to obtain a non-acid functional rosin reaction product.

The foregoing and other objects, features, and advantages will become more apparent from the following detailed description, which proceeds with reference to the accompanying figures.

BRIEF DESCRIPTION OF THE DRAWINGS

FIG. 1 shows curing reactions involving exemplified compounds.
FIG. 2 shows the $^1$H NMR spectra of several compounds.
FIG. 3 shows DSC thermograms of several compounds.
FIG. 4 is a graph depicting the degree of conversion vs. temperature at different heating rates for several compounds.
FIG. 5 is a graph depicting the effect of heating rate on reaction rate for several compounds.
FIG. 6 shows the $^1$H NMR spectra of several compounds.
FIG. 7 is a table showing DSC results of curing of one novel embodiment disclosed herein.
FIG. 8 is a table showing DSC results of curing of another novel embodiment disclosed herein.
FIG. 9 shows FT-IR spectra of several compounds disclosed herein.
FIG. 10 shows the $^1$H NMR spectra of a further novel compound disclosed herein.
FIG. 11 shows the $^1$H NMR spectra of another novel compound disclosed herein.
FIG. 12 shows DSC thermograms of several compounds.
FIG. 13 shows FT-IR spectra of several compounds disclosed herein.
FIG. 14 is a graph depicting the tensile properties of several compounds disclosed herein.

DETAILED DESCRIPTION

For ease of understanding, the following terms used herein are described below in more detail:

A "rosin acid" includes any acid compound naturally-occurring in rosin. Rosin acid can be used in the methods, compounds and compositions disclosed herein in a form of a purified or partially purified rosin acid isomer, or a component in the raw rosin material. In other words, it is not necessary to purify or isolate a rosin acid from raw rosin material in order to react the rosin acid as described herein. Rosin is a mixture of acidic (ca. 90%) and neutral (ca. 10%) compounds. The acidic components, generally named rosin (or resin) acids, are also a mixture containing mainly isomeric abietic-type acids (40-60%) and pimaric-type (9-27%) acids on the basis of total rosin weight. It is known to the art that pimaric type-acids can thermally and/or under catalytic conditions isomerize to yield abietic-type acids. Thus, as used herein the term "rosin acids" is also inclusive of a mixture of acids present in a rosin, that may be partially or completely isolated from a rosin, and/or enriched in abietic-type acids via thermal or catalytic conversion within a rosin. Rosin acids typically are characterized as including three fused $C_6$ rings that include at least one carboxyl group (e.g., carboxylic acid) and at least one unsaturated carbon-carbon double bound (e.g., a diene structure). The chemical reactivity of rosin acids resides in its monocarboxylic acid and the unsaturated carbon-carbon double bonds.

A "rosin acid moiety" refers to a polycyclic moiety present in naturally-occurring rosin acid. A rosin acid moiety can be from any of the isomers of rosin acid including abietic acid, neoabietic acid, dehydroabietic acid, palustric acid, pimaric acid, levopimaric acid, and isopimaric acid.

A "non-acid functional rosin" as used herein refers to a modified rosin acid wherein the carboxylic acid functional group(s) present in the original or naturally-occurring rosin structure has been chemically modified to yield a distinct chemical functional group that is non-acidic. In certain embodiments, "non-acidic" means that the distinct chemical functional group results in a structure with a pKa of greater than 7 in aqueous solution. It is to be understood that "non-acid functional rosin" is also inclusive of a molecule derived from rosin wherein at least one carboxylic acid functional group distinct from the carboxylic acid functional group present in the original or naturally-occurring rosin structure has been chemically linked to the structure (in this instance, the non-acid functional rosin structure may have a pKa of greater than 7 in aqueous solution).

A "non-acid functional rosin moiety" refers a rosin acid moiety that has been chemically modified to remove or convert the carboxylic acid group originally present in the rosin acid moiety.

Rosin-derived epoxides and rosin-derived curing agents for use in epoxy resin systems are disclosed herein. In certain aspects there are disclosed modified rosins wherein a rosin acid or a modified rosin is reacted with at least one functionalizing molecule. A "functionalizing molecule", as used herein, is a moiety that contains two reactive units, one reactive unit suitable for forming a chemical linkage to a rosin acid or a modified rosin and a second unit which may or may not be suitable for forming a chemical linkage to a second rosin acid or modified rosin. In those implementations wherein the second unit is not suitable for linkage to a second rosin acid the second unit will contain a group that either contains a reactive unit suitable for use in the curing reaction of an epoxy resin system or a group that can be converted to a reactive unit suitable for use in the curing reaction of an epoxy resin system. The product of the reaction with the functionalizing molecule may be a non-acid functional rosin structure or it may be a rosin structure that incorporates the chemical functional group(s) introduced by the functionalizing molecule.

In certain embodiments, a functionalizing molecule may react directly with a rosin acid to produce a non-acid functional rosin. For example, the functionalizing molecule may reduce the carboxylic acid group of the rosin acid to a hydroxyl group. In other examples, the functionalizing molecule may react with the carboxylic acid group of the rosin acid to convert the carboxylic acid into a corresponding ester group. In other embodiments, a functionalizing molecule may react with a modified rosin resulting in a non-acid functional rosin structure.

The functionalizing molecule comprises a chemical structure containing at least one reactive unit suitable for chemical linkage to a rosin acid. As noted above rosin acids contain two structural features: a monocarboxylic acid and the unsaturated carbon-carbon double bonds, that provide means for chemical reactivity. Thus the functionalizing molecule will contain at least one unit suitable for chemical reaction with either a monocarboxylic acid or the unsaturated carbon-carbon double bonds.

In certain embodiments the functionalizing molecule will contain two reactive units suitable for chemical linkage to a rosin acid. Here the reactive units of the functionalizing molecule may be the same or different. In certain implementations both reactive units may react with the monocarboxylic acid of the two respective rosin acids generating a non-acid functional "rosin dimer". In certain embodiments both reactive units may react with the unsaturated carbon-carbon double bonds of the two respective rosin acids generating an acid functional rosin dimer. In yet further embodiments one reactive unit may react with the unsaturated carbon-carbon double bonds of a first rosin acid and the second reactive unit may react with the monocarboxylic acid of a second rosin acid.

The functionalizing molecule will contain at least one unit suitable for chemical reaction with either a monocarboxylic acid or the unsaturated carbon-carbon double bonds. Reactive units suitable for reactivity with the monocarboxylic acid may comprise a chemical structure that contains a leaving group which provide an electrophillic center on the functionalizing molecule that initiates a reactivity with the acid functional oxygen atom of the carboxylic acid yielding an esterified, non-acid functional rosin. "Leaving groups" are chemical entities that when disassociated from a parent molecule result in a stable anion or neutral molecule. For illustrative purposes, halogenated hydrocarbons, particularly those examples containing heavy halogens (Cl, Br and I) are considered as molecules that include leaving groups. Here disassociation of the halogen from the hydrocarbon yields a stable anionic halogen and an electrophillic hydrocarbon suitable for reaction with an electron rich center (e.g. a carboxylic acid). Illustrative halogenated hydrocarbons include methyl iodide, methyl bromide and methyl chloride.

In other embodiments reactive units suitable for reactivity with the monocarboxylic acid may comprise a chemical structure that contains a nucleophile which provides an electron rich center on the functionalizing molecule that initiates a reactivity with the carbon atom of the carboxylic acid and eliminating the acid functional oxygen atom yielding a non-acid functional rosin. A nucleophile comprises an electron rich functional group (e.g. a strong base). For illustrative purposes a salt of an aliphatic alcohol (e.g., sodium methoxide or potassium ethoxide) is a strong nucleophile; the deprotonated alcohol contains an electron rich center on the oxygen atom capable of interaction with the carbon atom of the carboxylic acid of the rosin acid. Once the interaction occurs a chemical linkage can form which leads to elimination (e.g. release) of the hydroxyl group (OH—, the acid functional element) to yield an esterified, non-acid functional rosin.

Reactive units suitable for reactivity with the unsaturated carbon-carbon double bonds in conjugation with an electron withdrawing group generally comprise units suitable for Diels-Alder reactivity. The rosin and the Diels-Alder reagent can be reacted in a Diels Alder reaction under conditions well known in the art, such as between the melting point of the rosin and the boiling point of the Diels-Alder reagent. The reaction can be carried out at elevated pressure in order to increase the boiling point of the Diels-Alder reagent. Particularly suitable Diels-Alder reagents include maleic anhydride, glycidyl methacrylate, or unsaturated mono or di-carboxylic acids (e.g., acrylic acid) however more generally a reactive unit containing a double bond in conjugation with an electron withdrawing group. Other illustrative Diels-Alder reagents include 3,4,5,6-tetrahydrophthalic anhydride, dimethylmaleic anhydride, aconitic anhyrided, citraconic anhydride, 2,3-dichloromaleic anhydride, methacrylic anhydride, maleic acid, crotonic acid, glutaconic acid, and 3,3-dimethylacrylic acid.

In certain implementations the functionalizing molecule may react with the unsaturated carbon-carbon double bonds of a non-acid functional rosin to yield a rosin containing an anhydride functional group suitable for use as a curing agent.

In certain embodiments the anhydride of a rosin curing agent can be further reacted to provide for different properties. The anhydride can be hydrolyzed to yield a modified rosin that contains three carboxylic acid groups—two that derive from the hydrolysis of the anhydride and one from the parent rosin acid. In yet further embodiments the carboxylic acids can be reacted with an epoxide-containing moiety to yield a non-acid functional rosin with more than one epoxide suitable for use as a non-acid functional rosin epoxide curing agent. Illustrative compounds that include an epoxide-containing moiety include 2-(bromomethyl)oxirane, 2-(chloromethyl)oxirane, epichlorohydrin, epifluorohydrin, glycidol, and glycidamide. Alternatively the anhydride of a modified non-acid functional rosin can be reacted with a functionalizing molecule wherein one of the units comprises a primary amine. In other embodiments, the carboxylic acid group of a rosin acid, which rosin acid may have initially been modified with a first functional molecule such a Diels-Alder reagent, can be reacted with a second functionalizing molecule that includes at least one primary amine resulting in a non-acid functional rosin structure. Illustrative compounds that include a primary amine include an alkane diamine (e.g., ethane, -1,2-diamine; or propane, -1-2-diamine); 2-(2-aminopropoxy)propan-1-amine; 2-(2-(2-aminopropoxy)propoxy)propan-1-amine; 4,4-methylenedicyclohexanamine; aniline; 4,4'methylenediamine; 4-aminobenzoic acid; 1,4-diaminonaphthalene; 2,3,5,6-tetramethyl-p-phenylenediamine; 1,4-bis(3-aminopropoxy)butane; 4,4'-oxydianiline; 2,7-diaminofluorene; triethylenetetramine; N,N'-bis(2-aminoethyl)-1,3-propanediamine; m-xylylendiamine; and tetraethylenepentamine.

Also disclosed herein are rosin-derived epoxies synthesized with rosin acid as a reactant, and including one or more rosin acid moieties and two or more glycidyl ether or glycidyl ester moieties in their chemical structure. In certain embodiments, the rosin-derived epoxies are small molecules (i.e., non-polymeric) that serve as monomers for an epoxy resin system. For example, the glycidyl ether and/or glycidyl ester moieties can be cured with a curing agent to produce a cured, polymeric material.

Also disclosed herein are rosin-derived curing agents synthesized with rosin acid as a reactant, and including one or more rosin acid moieties and one or more of the following functional groups: anhydride, carboxylic acid (the modifying carboxylic acid is in a different position compared to the carboxylic acid group present in the naturally-occurring unmodified rosin acid), amine or polyamine. In certain embodiments, the rosin-derived curing agents are non-acid functional rosins.

The rosin-derived epoxies or the rosin-derived curing agents may also include a bridge moiety R that covalently bonds together two rosin acid moieties.

As described above, the synthetic processes disclosed herein utilize the reactive carboxyl group and the reactive diene group of a rosin acid. For example, the carboxyl group may be reduced to a hydroxyl group that is then converted into a glycidyl ether group. The diene group of the rosin acid moiety may be reacted (before or after etherification) with a modifying moiety (e.g., a bridging moiety R) to introduce properties of the modifying agent into the resulting rosin-derived epoxide.

For illustrative purposes a number of structures are presented below.

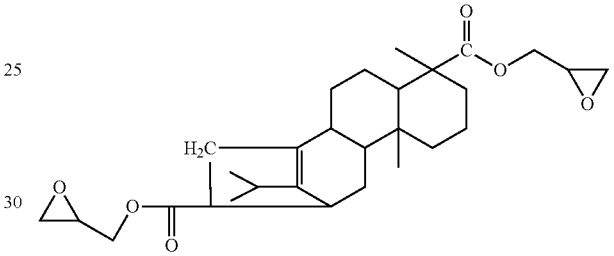

Structure 1

Structure 1 is an example of a non-acid functional rosin epoxide agent. Here a functionalizing molecule is a Diels-Alder reactive group that contains a carboxylic acid. Subsequent to reaction with the Diels-Alder reactive group the modified rosin contains two acid functional carboxylic acids which can subsequently be reacted with an epoxide-containing moiety (e.g. epichlorohydrin) to yield a non-acid functional rosin epoxide agent suitable for use in an epoxy resin system.

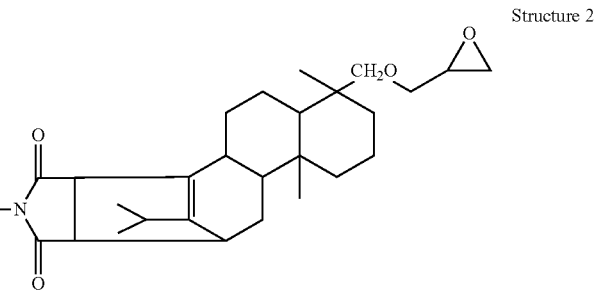

Structure 2

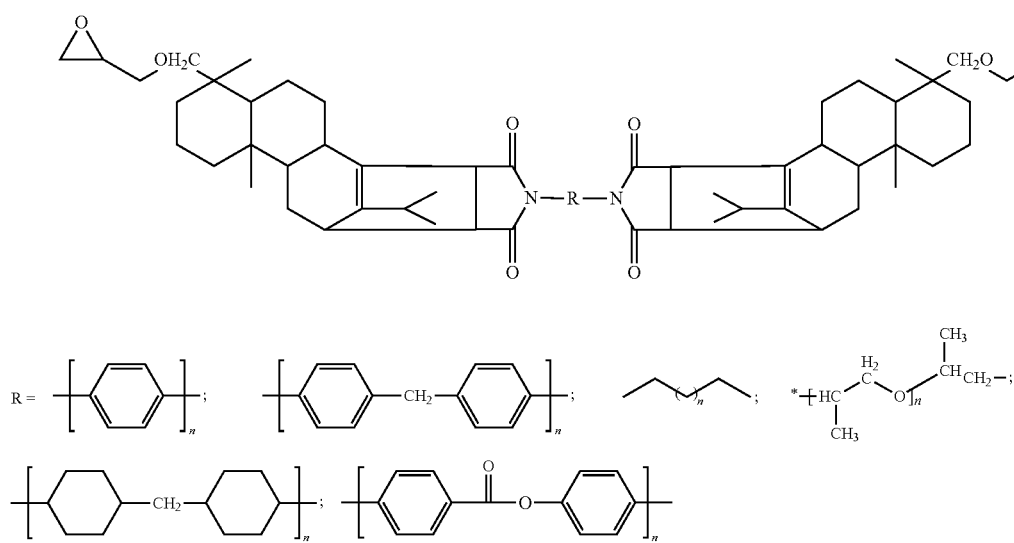

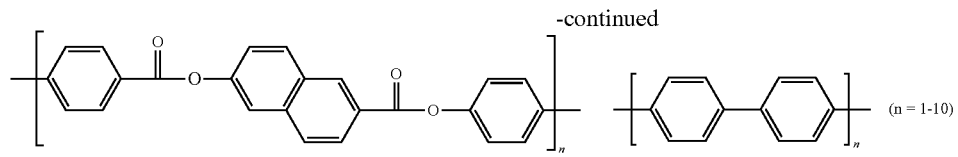

Structure 2 is an example of a non-acid functional rosin dimer epoxide which can be prepared through the introduction of an epoxide moiety (e.g., epichlorohydrin) to a rosin acid to yield a non-acid functional rosin that is subsequently reacted with a Diels-Alder reagent (e.g., maleic anhydride). The anhydride-containing non-acid functional rosin may then be reacted with a functionalizing molecule that includes a repeating unit that terminates with a primary amine.

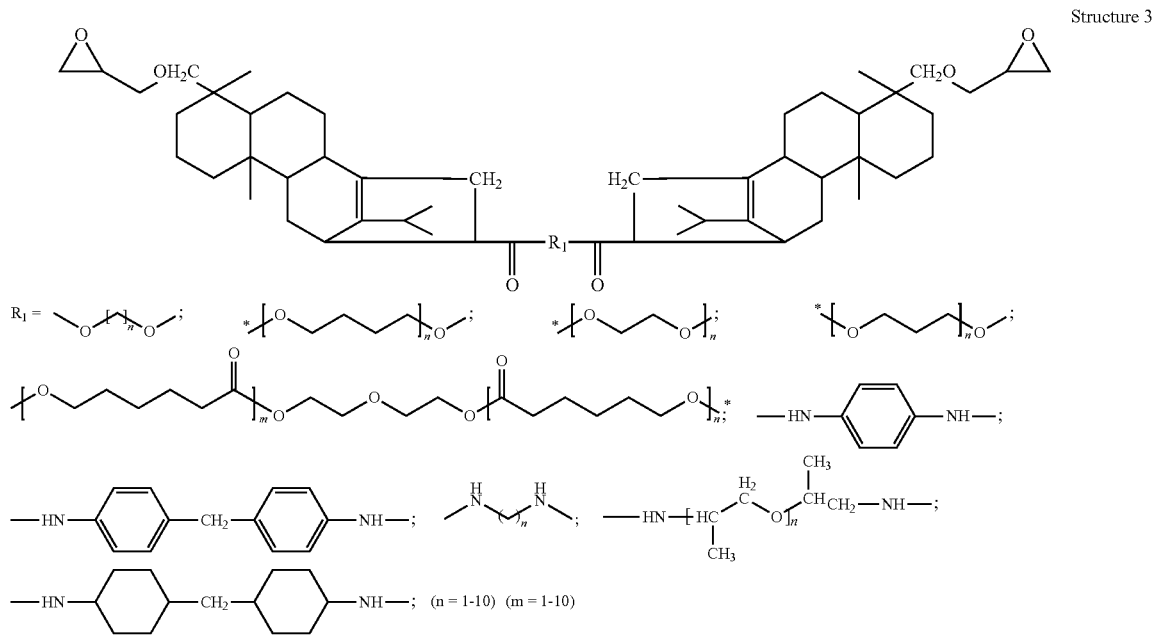

Structure 3 is an example of a non-acid functional rosin dimer epoxide that can be prepared through the introduction of an epoxide moiety (e.g., epichlorohydrin) to a rosin acid to yield a non-acid functional rosin that is subsequently reacted with a Diels-Alder reagent (e.g., acrylic acid). The acrylated non-acid functional rosin may then be reacted with a functionalizing molecule that includes a repeating unit that terminates with nucleophiles.

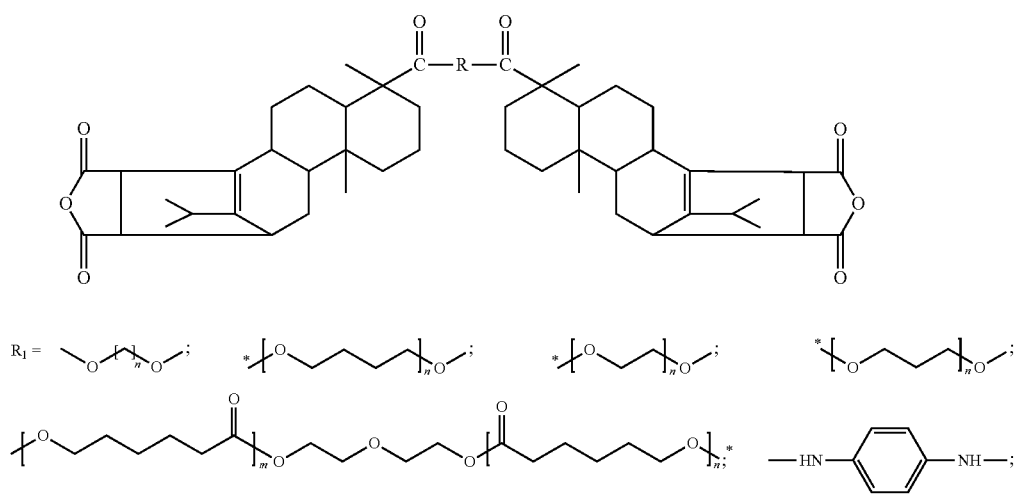

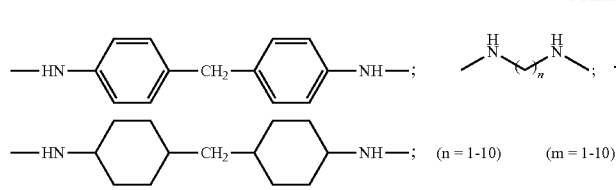
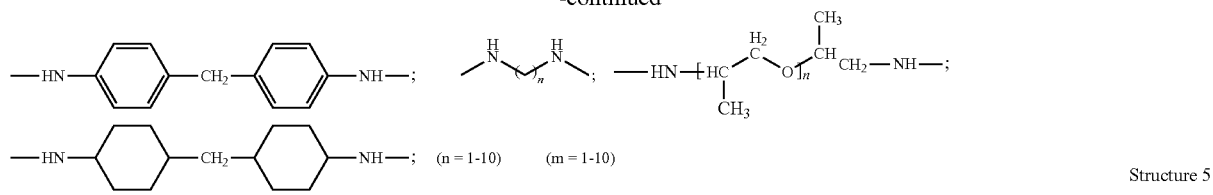

Structure 5

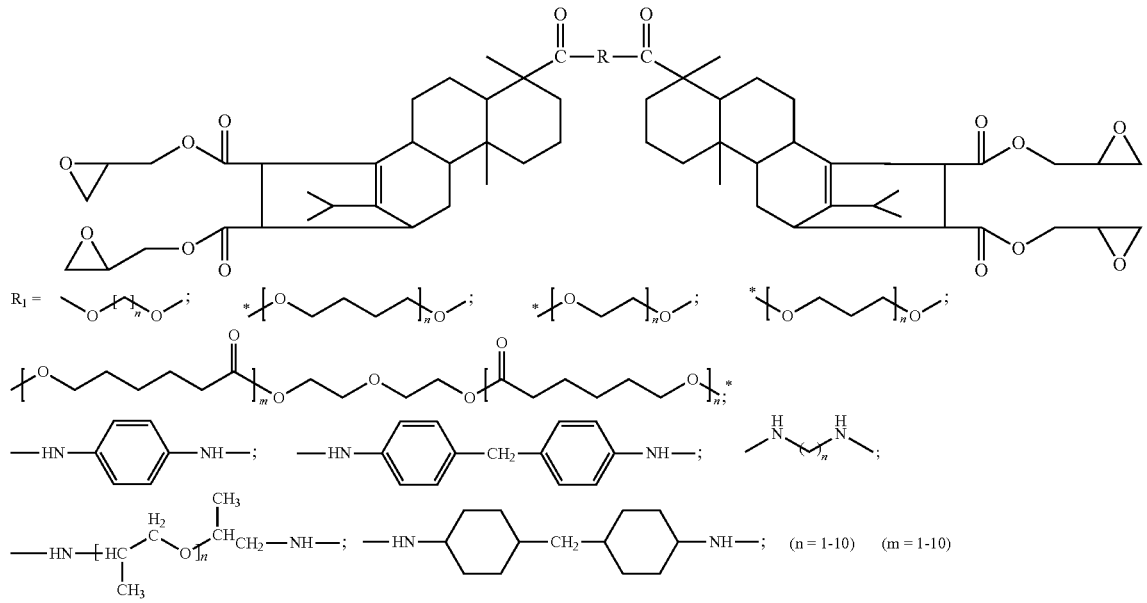

Structure 5 is an example of a non acid functional rosin dimer poly epoxide which can be prepared first through the introduction of a functionalizing molecule that terminates with nucleophiles to yield a non-acid functional rosin dimer which can subsequently be reacted with a Diels-Alder reactive group (e.g. maleic anhydride) to yield a non-acid functional rosin dimer curing agent (Structure 4). In certain implementations the non-acid functional rosin dimer curing agent can be hydrolyzed to yield four carboxylic acid groups which can then be reacted with an epoxide moiety (e.g. epichlorohydrin) to yield a non-acid functional rosin dimer poly epoxide agent (Structure 5).

Structure 6

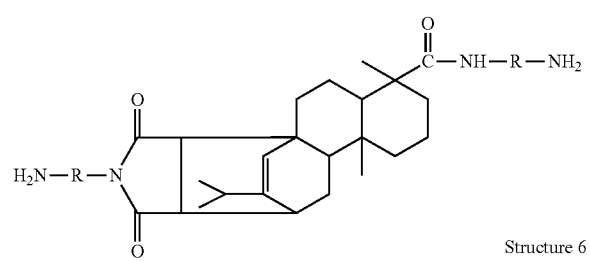

Structure 7

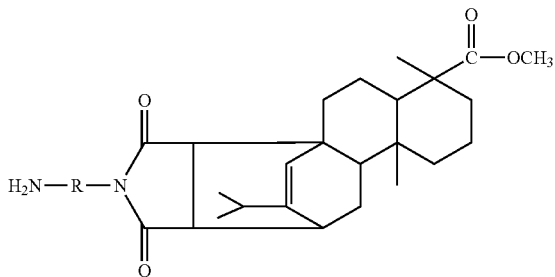

-continued

Structure 8

Structure 9

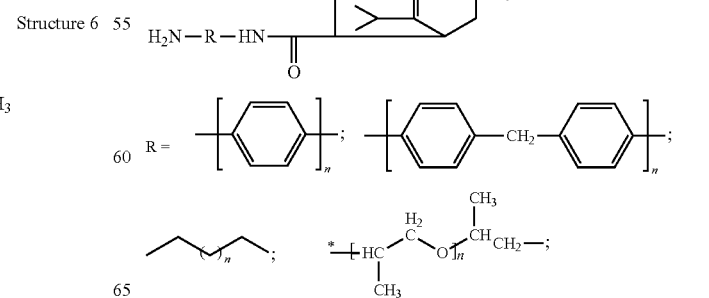

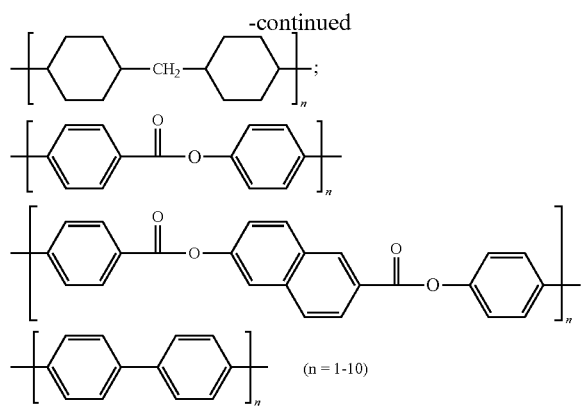

(n = 1-10)

Structures 6-9 are illustrative non-acid functional rosin curing agents. Structures 6 and 8 can be prepared via the reaction of the carboxylic acid on the rosin with a nucleophile (e.g. sodium methoxide) to yield a non-acid functional rosin which can subsequently be reacted with a Diels-Alder reactive group (e.g. maleic anhydride) to yield curing agent 6. Further reaction of curing agent 6 with a functionalizing molecule that terminates with amines yields a non-acid functional rosin curing agent 8. It is important to note that if the scheme to produce structure 8 were modified to eliminate the first step (the reaction with a nucleophile to eliminate the carboxcylic acid on the rosin) the result of the syntheses would be a distinct compound wherein a second functionalizing molecule would react with the carboxylic acid on the rosin to yield a non-acid functional rosin curing agent (structure 7). To generate structure 9, a rosin acid be reacted with a Diels-Alder reactive group (e.g. acrylic acid) which upon further reaction with a functionalizing molecule that terminates with amines yields a non-acid functional rosin curing agent 8.

anhydride) to yield a rosin anhydride which in the case of structure 10 is hydrolysed and then reacted with epoxide moiety (e.g. epichlorohydrin) to yield a non-acid functional rosin poly epoxide agent (Structure 10). In the case of structure 11 the rosin anhydride can be reacted with a functionalizing molecule containing a primary amine and carboxylic acid to yield a rosin derived structure with two carboxylic acid groups which can then be reacted with epoxide moiety (e.g. epichlorohydrin) to yield a non-acid functional rosin poly epoxide agent (Structure 11).

The curing agents used herein can be used to cure any type of epoxy resin systems. The epoxide agents disclosed herein can be used as monomers (or modifiers) for the backbone of any type of epoxy resin systems. In certain embodiments, the curing agents and epoxide agents disclosed herein may be a solid at room temperature. The solids can be in the form of a powder that can be used to make epoxy powder coatings.

EXAMPLES

According to one example, abietyl glycidyl ether and methyl maleopimarate were synthesized from one of the rosin acids. Abietyl glycidyl ether was used as a model compound representing rosin-based epoxies, while methyl maleopimarate was used as a model compound representing rosin-based anhydride curing agents. The synthesis methods of the model compounds were examined and the chemical structures were confirmed by $^1$H NMR, $^{13}$C NMR, FT-IR and ESI-MS. Curing of abietyl glycidyl ether with aniline and curing of methyl maleopimarate with phenyl glycidyl ether were investigated separately. Nonisothermal curing of the model systems was studied by DSC, and the cured products were characterized by $^1$H NMR.

General

Abietic acid (75% by HPLC) was obtained from Aldrich and used as received. It was actually a mixture of abietic acid

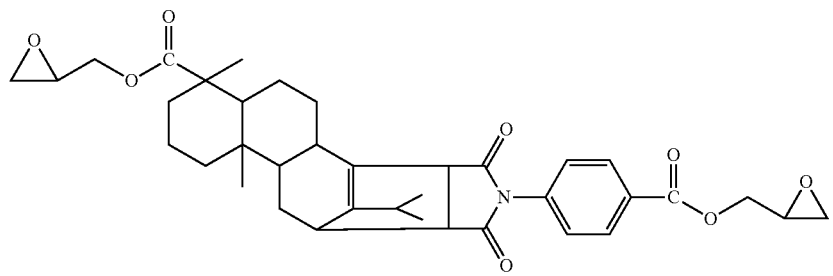

Structure 10

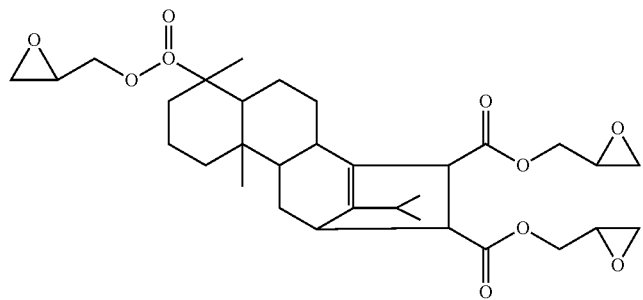

Structure 11

Structures 10 and 11 are a non-acid functional rosin poly epoxide agents which can be prepared through the reaction of a rosin acid with a Diels-Alder reactive group (e.g. maleic and other rosin acids with most neutral rosin compounds removed. Maleic anhydride (powder, 95%), iodomethane (99.5%), epibromohydrin (98%), hydroquinone (99%), phenyl glycidyl ether (99%) and 2-ethyl-4-methylimidazole (95%), aniline (99.5%) were also obtained from Aldrich. Lithium aluminum hydride (95%) was obtained from ACROS. Tetra-n-butylammonium hydrogen sulphate (97%) was obtained from Lancaster. Sodium hydroxide (99%, pellet), potassium carbonate (99%, anhydrous, granular) were obtained from B. T. Baker. Magnesium sulfate (anhydrous, reagent grade) was obtained from Fisher, as were all organic solvents (analytical grade). Solvents for synthesis (methanol, xylene, toluene, THF, DMF) were dried with 5 Å molecular sieves before use; the others (ethyl ether, chloroform) were used as received. TLC was performed on silica gel/UV$_{254}$ (0.25 mm, Sorbent Technology) plates. Column chromatography was carried out with Merck Kieselgel 60 (0.040-0.063 mm). $^1$H NMR and $^{13}$C NMR spectra were recorded with a Bruker 300 MHz spectrometer at room temperature in deuterated chloroform (CDCl$_3$). Chemical shifts are reported relative to chloroform (δ7.26) for $^1$H NMR and chloroform (δ77.28) for $^{13}$C NMR. FTIR spectra were recorded with NEXUS 670 FT-IR, KBr pellet, wavelength from 4000 to 400 cm$^{-1}$. Mass spectrum was recorded with a LCQ Advantage ESI mass spectrometer. Gum resin was obtained from Sigma. Polycaprolactone diol (M$_n$=530), maleic anhydride (95%), p-toluenesulfonic acid monohydrate (99%), zinc oxide (nanopowder), 2-ethyl-4-methylimidazole (95%) were obtained from Aldrich. Phosphoric acid (85%) was obtained from Fisher. Epoxide DER 332E (2,2-Bis[4-(glycidyloxy)phenyl]propane) was provided by Dow chemical company and the epoxide equivalent weight is 171-175 g/eq. All chemicals were used as received.

Synthesis of Compounds

Example

Non-Acid Functional Rosin Expoxide Agent

Scheme 1.
Synthesis route for a non-acid functional rosin derived epoxide agent

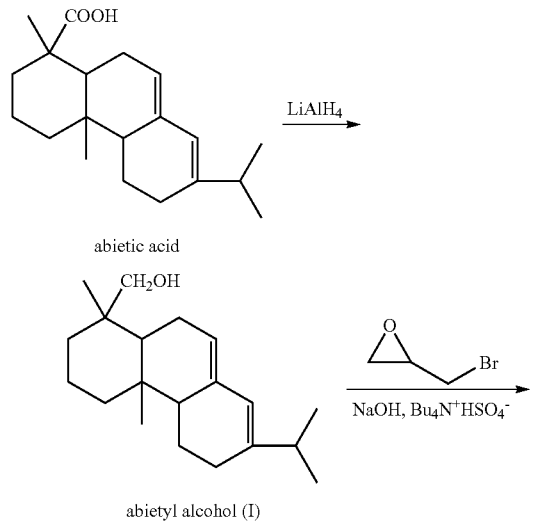

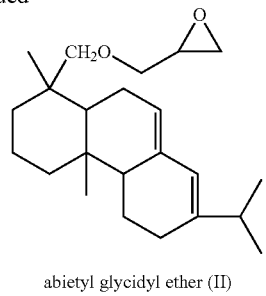

abietyl glycidyl ether (II)

The glycidyl ether of abietic alcohol was synthesized as an analog to rosin-based epoxies. Although not bound by any theory, it is believed that the ether linkage is more resistant to hydrolysis and thermolysis compared to an analogous ester linkage. The carboxyl group of rosin acid was first reduced to a hydroxyl group which was then reacted with epihalohydrin to achieve the glycidyl ether.

To reduce the carboxyl group of rosin to a hydroxyl group, LiAlH$_4$ was used as the reducing agent (Scheme 1). The resulting abietyl alcohol intermediate (I) was then reacted with epibromohydrin to form abietyl glycidyl ether (II) in the presence of a phase transferring catalyst Bu$_4$N$^+$HSO$_4^-$. Because of the steric hindrance effect of the fused ring on the hydroxyl methyl group of abietyl alcohol, using epichlorohydrin only resulted in a very low yield of the glycidyl ether. By using the more reactive epibromohydrin, the etherification was able to proceed with a better yield. The yield and recovery yield of the epoxide from the two-step reaction were 29% and 87%, respectively.

1) Abietyl Alcohol (I): Reduction of a Rosin Acid to Yield a Non-Acid Functional Rosin Abietic acid (2.00 g, 75% purity, 5 mmol) in dry THF (60 mL) was added dropwise to a suspension of powdered LiAlH$_4$ (1.12 g, 29.4 mmol) in dry THF (30 mL) at room temperature. The reaction mixture was stirred overnight at room temperature. To this mixture was added 60 mL water and 50 mL H$_2$SO$_4$ (1M), stirring for 1 h. The mixture was extracted with ethyl ether (60 mL×3). After drying with anhydrous MgSO$_4$ and evaporating the solvent, the residue was purified by silica gel column chromatography (AcOEt:hexane=13:87) to yield the product (1, 1.38 g, yield 96.5%). $^1$H NMR δ5.77 (s, 1H), 5.40 (s, 1H), 3.36 (m, 1H), 3.13 (m, 1H), 2.17-1.83 (m, 9H), 1.37-1.22 (m, 5H), 1.03-1.01 (m, 7H), 0.75-0.41 (m, 7H). $^{13}$C NMR δ145.47, 135.77, 122.60, 121.13, 72.35, 50.99, 43.88, 39.09, 37.72, 35.93, 35.11, 34.86, 27.75, 24.05, 22.90, 21.66, 21.10, 18.40, 17.93, 14.47. FT-IR ν889, 1050, 1300, 1380, 1470, 2960, 3390 cm$^{-1}$. ESI-MS m/z 289.2, [M+H$^+$]

2) Abietyl Glycidyl Ether (II) Etherification of a Non-Acid Functional Rosin Epoxide Containing Agent Abietyl alcohol (I) (527 mg, 1.8 mmol) was dissolved in toluene (10 mL) at room temperature. To this solution were added powdered NaOH (146 mg, 3.6 mmol) and Bu$_4$N$^-$HSO$_4^-$ (186 mg, 0.5 mmol). The mixture was stirred for 0.5 h at room temperature and then epibromohydrin (600 mg, 4.4 mmol) was dropped in. The mixture was further stirred overnight at 60° C. and cooled to room temperature. The reaction was quenched with H$_2$O (20 mL) and the mixture was extracted with ethyl ether (30 mL×3). After drying with anhydrous MgSO$_4$ and removing the solvent under reduced pressure, the product was purified by silica gel column chromatography (AcOEt: hexane=1:9). [II, 200 mg, yield 30% (yield based on recovering start material 90%)]. $^1$H NMR δ5.77 (s, 1H), 5.40 (s, 1H), 3.65 (m, 1H), 3.36-2.92 (m, 4H), 2.76 (m, 1H), 2.57 (m, 1H), 2.21-1.20 (m, 12H), 1.02-0.98 (m, 8H), 0.88-0.81 (m, 7H). $^{13}$C NMR δ145.16, 135.42, 122.44, 121.24, 80.92, 72.03, 51.08, 50.69, 44.24, 43.89, 38.80, 37.25, 36.37, 34.88, 34.63, 27.54, 23.99, 22.66, 21.42, 20.86, 18.22, 18.03, 14.23. FT-IR ν768, 883, 893, 922, 1110, 1260, 1380, 1470, 1740, 2960 cm$^{-1}$. ESI-MS m/z 345.2, [M+H$^+$]; 367.2, [M+Na$^+$].

Example

Non Acid Functional Rosin Curing Agent

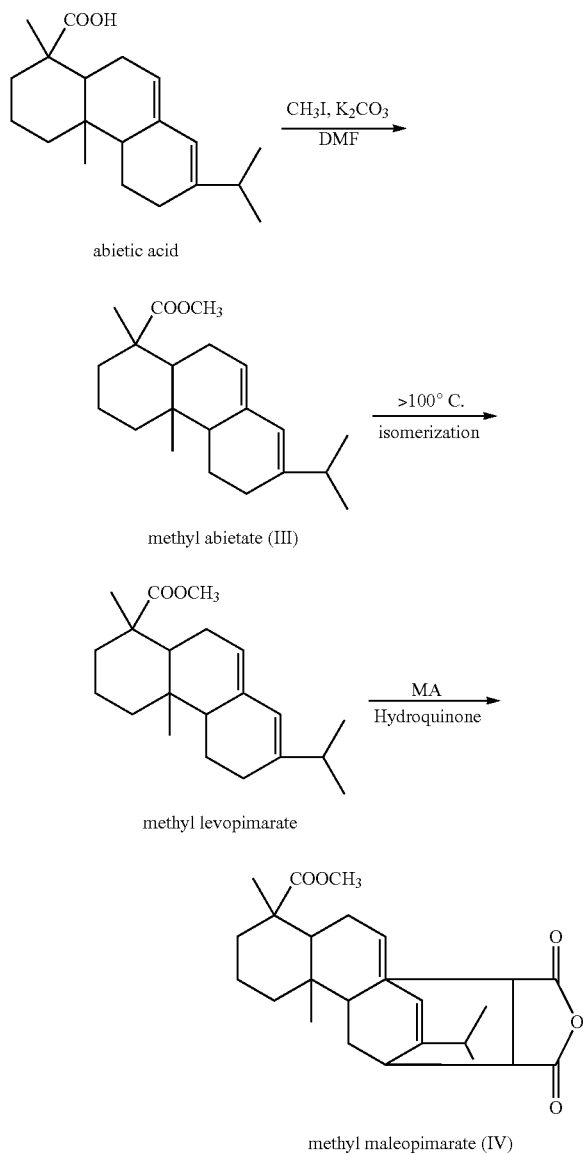

Scheme 2. Synthesis route for a non-acid functional rosin curing agent

3) Methyl Abietate (III) Esterification of a Rosin Acid to Yield a Non-Acid Functional Rosin Powdered K$_2$CO$_3$ (5.75 g, 42 mmol) was added to anhydrous DMF (60 mL) and the mixture was stirred for 5 minutes at 25° C. To this mixture was added abietic acid (5.00 g, 75% purity, 12 mmol) and then iodomethane (11.40 g, 60 mmol). The reaction was stirred for 4 hr at 25° C. and the solid precipitate was removed via filtration. The filtrate was diluted with 300 mL ethyl ether, and then washed with water (3×100 mL). The ethyl ether layer was then dried with anhydrous MgSO$_4$ and concentrated in vacuum. Purification was carried out by silica-gel column chromatography (EtOAc:hexane=1:9) to provide methyl abietate (III, 3.00 g, yield 77%). $^1$H NMR δ5.77 (s, 1H), 5.36 (s, 1H), 3.62 s, 3H), 2.23-1.56 (m, 11H), 1.25-1.18 (m, 6H), 1.02-1.00 (m, 7H), 0.80 (s, 3H). $^{13}$C NMR δ179.20, 145.52, 135.74, 122.56, 120.84, 52.06, 51.15, 46.81, 45.32, 38.55, 37.33, 35.11, 34.75, 27.70, 25.90, 22.69, 21.64, 21.08, 18.36, 17.24, 14.26. FT-IR ν897, 1150, 1230, 1250, 1390, 1460, 1730, 2960 cm$^{-1}$. ESI-MS m/z 317.6, [M+H$^+$]; 339.6, [M+Na$^+$].

4) Diels-Alder Reaction of a Non-Acid Functional Rosin Acid to Yield a Non-Acid Functional Rosin Curing Agent For the preparation of an analog to the rosin-based anhydride hardeners, the free carboxyl groups of rosin were first blocked by esterification (Scheme 2) with CH$_3$I in DMF, using K$_2$CO$_3$ as the catalyst. Similar to the above etherification, the fused ring also had a significant steric hindrance effect on the reaction of the carboxyl group. Maleic anhydride was added onto the methyl ester of abietic acid (III) through Diels-Alder reaction, using hydroquinone as the catalyst. It was known that levopimaric acid was the only rosin acid which could undergo Diels-Alder adduction, and the other isomeric rosin acids experienced the isomerization to levopimaric acid at elevated temperatures during the reaction. The yield of rosin-based anhydride (IV, methyl maleopimarate) from the two-step reaction was 66%. Using H$_3$PO$_4$ as a catalyst in the Diels-Alder reaction could also achieve the final product, but resulted in a lower yield (54%) from the two-step reaction. The structures of the intermediate and final products were identified by $^1$H NMR. FIG. 4 gives the $^1$H NMR spectra of abietic acid, abietyl glycidyl ether and methyl maleopimarate. Chemical shift peaks from δ0.6 to 2.2 were attributed to the protons of six-member fused rings of rosin.

5) Methyl Maleopimarate (IV) Diels-Alder Reaction of a Non-Acid Functional Rosin to Yield a Non-Acid Functional Rosin Curing Agent Methyl abietate (III) (3.00 g, 9 mmol), maleic anhydride (1.76 g, 18 mmol) and hydroquinone (0.02 g, 0.18 mmol) were mixed in a sealed tube in dry xylene (10 mL). The mixture was stirred at 220° C. for 5 h under Ar protection. The reaction was cooled to 80° C., and the reaction solution was transferred into a beaker. Most of the product precipitated itself as crystals with the cooling down of the solution and was collected with a funnel. The residual product in the filtrate was precipitated with ethyl ether (50 mL) and collected by filtration. Then the two solid parts were combined and washed with 200 mL ethyl ether, dried to obtain the pure product (IV, 3.2 g, yield 86%). $^1$H NMR δ5.53 (s, 1H), 3.67 (s, 3H), 3.11 (m, 2H), 2.72 (d, 1H), 2.50 (m, 1H), 2.25 (m, 1H), 1.78-1.24 (m, 13H), 1.15 (s. 3H), 1.00-0.98 (d, 6H), 0.59 (s, 3H). $^{13}$C NMR δ179.32, 172.97, 171.26, 148.31, 125.34, 53.51, 53.47, 52.27, 49.64, 47.30, 45.87, 40.67, 38.21, 37.89, 36.90, 35.88, 35.00, 32.99, 27.42, 21.85, 20.79, 20.17, 17.20, 16.95, 15.76. FT-IR ν795, 850, 922, 945, 1000, 1090, 1140, 1240, 1390, 1470, 1720, 1790, 1860, 2880, 2960 cm$^{-1}$. ESI-MS m/z 415.4, [M+H$^+$].

Example

Non-Acid Functional Rosin Epoxide Agents Containing Multiple Epoxides

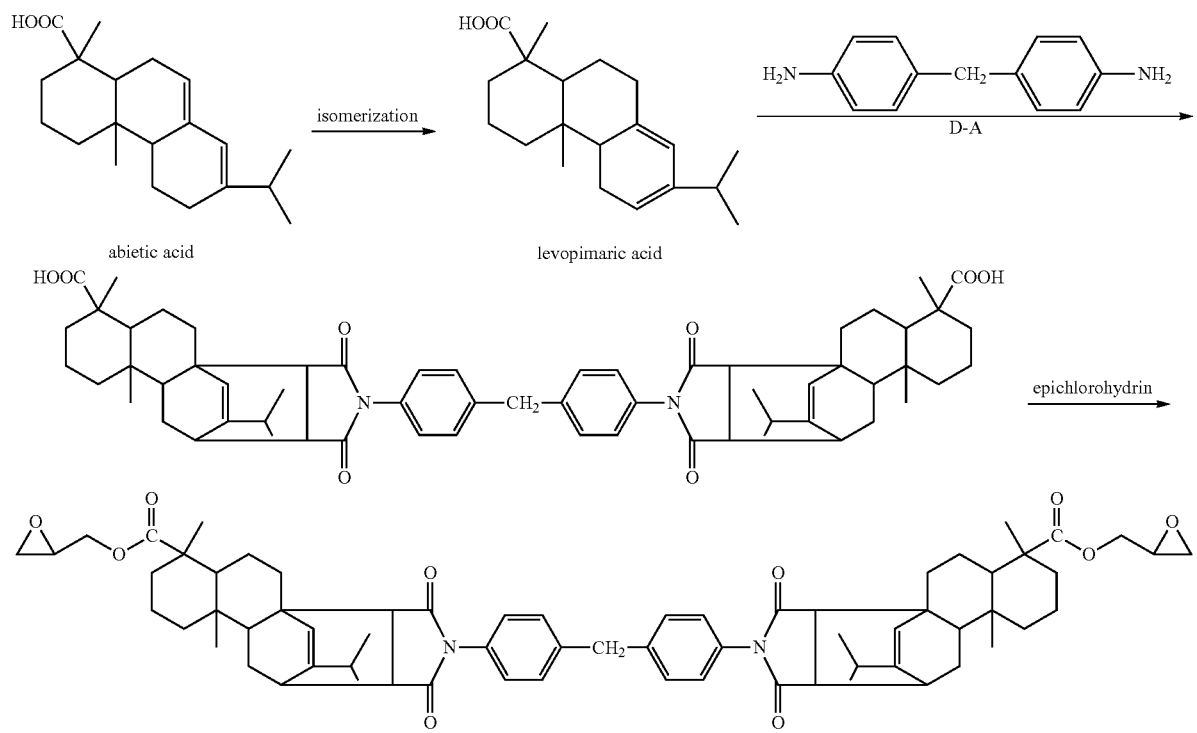

Scheme 3. Synthesis route for a non-acid functional rosin derived epoxide agents containing multiple epoxides 1) Diels-Alder Reaction Between a Rosin Acid and a Diels-Alder Reagent Rosin-maleic anhydride imidodicarboxylic acid (RMID) was made from maleopimaric acid following the procedures described by Liu in *Polym Int* 55:545-551 (2006). $H^1$-NMR [DMSO, ppm]: 7.97-8.0 (2H), 7.18-7.21 (2H), 5.49 (1H), 3.10-3.06 (2H), 2.68-2.72 (1H); $^{13}$C-NMR (DMSO, ppm) 180.34, 177.77, 176.76, 147.22, 136.44, 130.59, 127.34, 124.81. FT-IR (cm$^{-1}$) 1708, 1776. ESI-MS m/z, 520.5 [M+H$^+$].

2) Reaction of a Modified Rosin with an Epoxide Containing Moiety to Yield a Non-Acid Functional Rosin In a 100 mL three-necked round flask equipped with a magnetic stirrer, 2.6 g (0.005 mol) RMID was dissolved in 60 mL DMF, followed by gradual addition of 0.3 g (0.0125 mol) sodium hydride under the protection of Ar. After this mixture was stirred at room temperature for 2 h, 4.63 g (0.05 mol) epichlorohydrin was added. The reaction was brought to 150° C. and continued for another 5 h. It was cooled to room temperature and the solid precipitate was removed via filtration. The filtrate was diluted with 100 mL ethyl ether and washed with 50 mL water three times. The upper ether layer was dried with anhydrous magnesium sulfate and concentrated by a rotary evaporator, giving 1.48 g yellowy powder. (yield: 47%). $^1$H-NMR (CD$_3$Cl, ppm) 8.06-8.09 (2H), 7.22-7.25 (2H), 5.49 (1H), 4.59-4.63 (1H), 4.48-4.39 (1H), 4.10-4.16 (1H), 3.82-3.89 (1H), 3.30 (1H), 3.10-3.06 (1H), 2.52-2.86 (6H). $^{13}$C-NMR (CD$_3$Cl, ppm) 178.57, 177.33, 176.16, 165.56, 147.63, 136.47, 130.69, 129.46, 126.41, 124.77, 65.78, 65.31. FT-IR (cm$^{-1}$) 853, 901, 1100, 1178, 1705, 1778. ESI-MS m/z, 632.9 [M+H$^+$].

Example

Acid Functional Linked Rosin Curing Agent

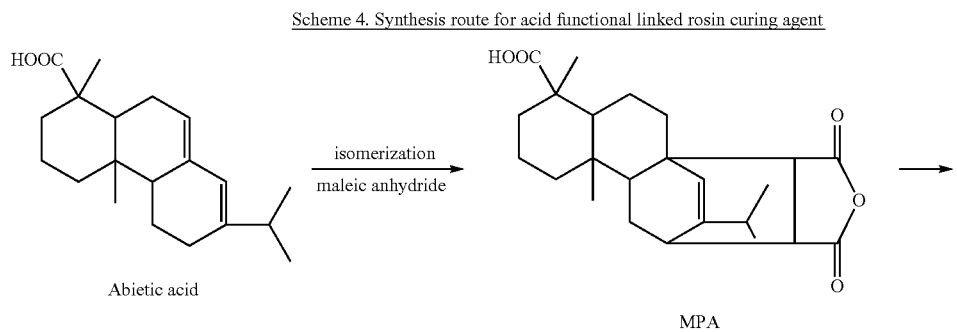

Scheme 4. Synthesis route for acid functional linked rosin curing agent

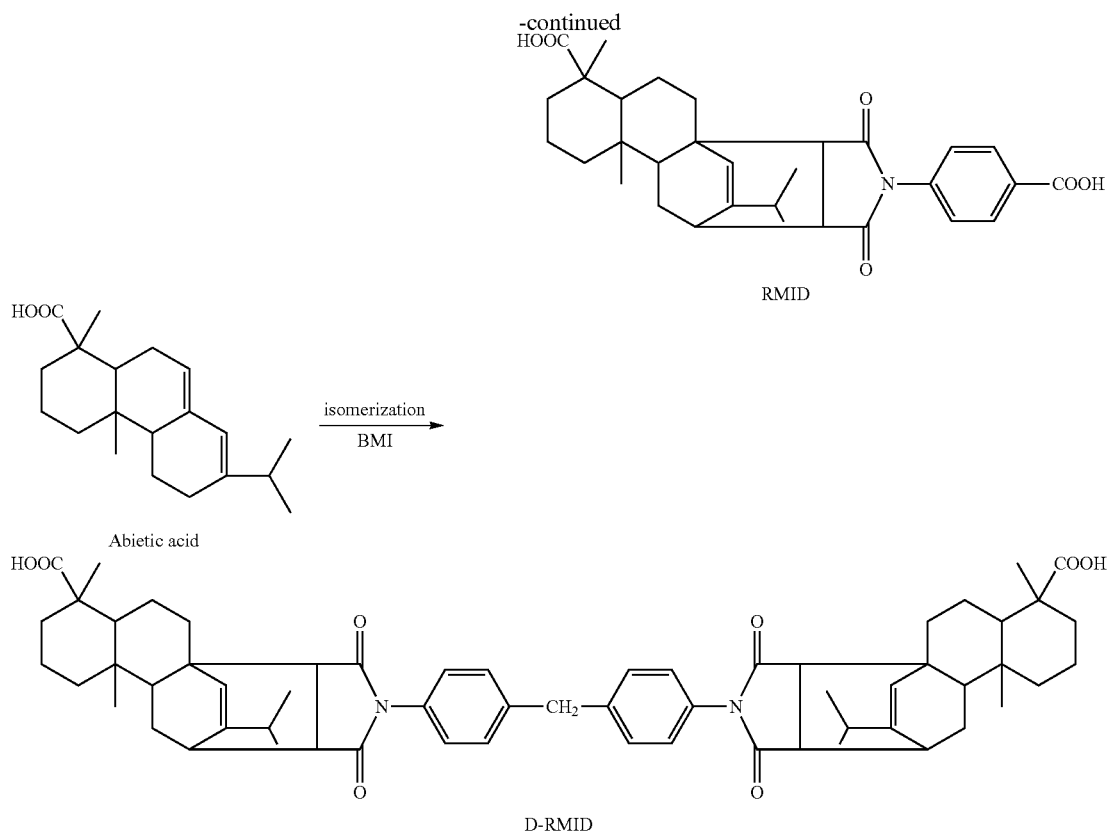

RMID

Abietic acid

D-RMID

1) Synthesis of Dirosin-Maleic Anhydride Imidodicarboxylic Acid (D-RMID)

In a 100 mL three-necked round flask equipped with a magnetic stirrer and reflux condenser, 10 g abietic acid (24 mmol) was heated to 180° C. and maintained at this temperature for 3 h to complete the isomerization from the abietic structure to the pimaric structure under the protection of Ar. The reaction was cooled to 120° C., and 30 mL of acetic acid was added. To this mixture, 4.3 g 1,1'-(methylenedi-4,1-phenylene)bismaleimide (BMI, 12 mmol) and 0.46 g p-toluene sulfonic acid (PTS) (0.24 mmol) was added and the reaction was refluxed for 12 h before it was cooled to room temperature. The precipitate was collected via filtration and purified by several reprecipitations from warm chloroform to hexane. At last, the yellowy powder was dried in the vacuum oven at 70° C. for 12 h and the pure product weighting 10 g was obtained (yield: 87%). $H^1$NMR (DMSO-$d_6$, δ ppm): 7.26-7.29 (d, 4H), 6.94-6.97 (d, 4H), 5.47 (s, 2H), 3.95 (s, 2H), 2.97-3.0 (m, 2H), 2.66-2.71 (d, 2H), 2.32-2.43 (m, 2H), 2.11-2.18 (m, 2H), 1.63-1.17 (m, 26H), 1.06 (s, 6H), 0.92-0.96 (d, 12H), 0.51 (s, 6H); $^{13}$C-NMR (DMSO-$d_6$, δ ppm): 180.35, 177.79, 176.78, 147.38, 136.76, 131.04, 130.72, 127.36, 125.10, 53.92, 52.61, 49.54, 46.59, 45.80, 40.58, 38.44, 37.82, 36.92, 35.64, 32.99, 27.75, 22.05, 20.79, 20.13, 17.20, 16.92, 15.76. FT-IR (cm$^{-1}$) 752, 917, 948, 1011, 1076, 1082, 1232, 1381, 1445, 1602, 1649, 1704, 1783, 2870, 2930, 3000-3500.

Synthesis of a Non-Acid Functional Linked Rosin Curing Agent Acid from a Rosin Acid Scheme 5. The synthetic route of polyster anhydride

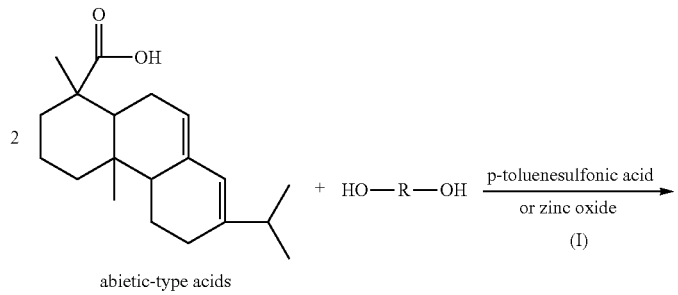

abietic-type acids

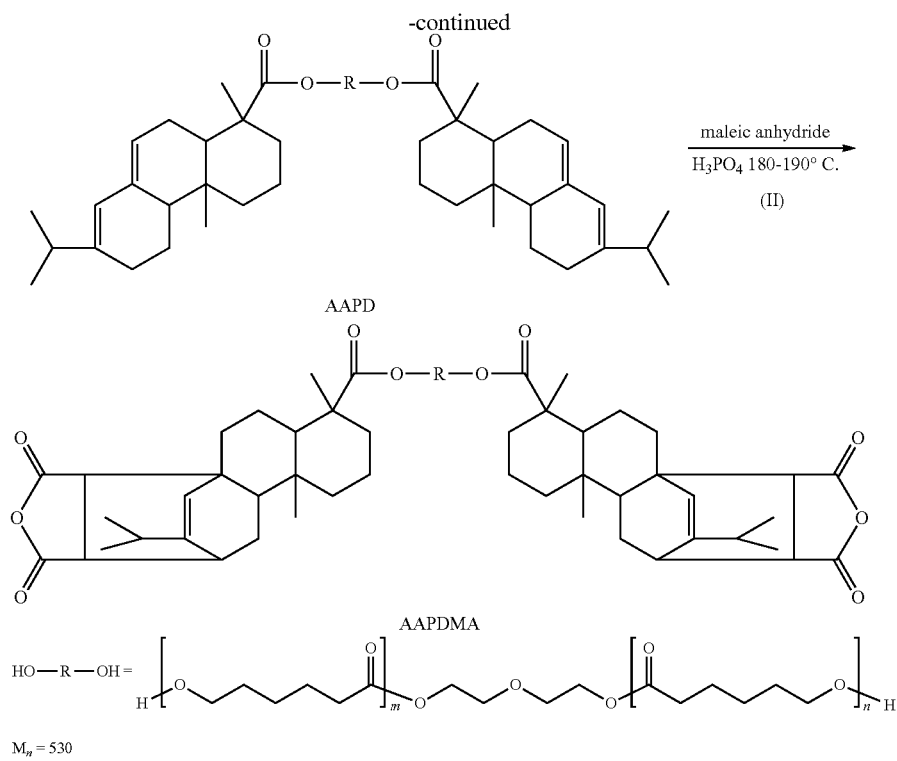

1) Procedure for the Esterification of Abietic Acid with Polycaprolactone Diol

A 250 ml flask equipped with a stirrer, a thermometer and a Dean-Stark trap under argon atmosphere was charged with 20 g gum rosin, 16.2 g polycaprolactone diol and 0.2 g p-toluenesulfonic acid (or 0.1 g nano zinc oxide). The flask was heated slowly to 230-240° C., and the mixture was stirred for 5 hours before it was cooled to 200° C. After that the system was applied to vacuum (3 mmHg) to remove the unreacted impurities. Then the resulted crude material (Chemical 2 in Scheme 5, named AAPD) was cooled down to room temperature and used for next step directly without further purification.

2) Dies-Alder Reaction of a Non-Acid Functional Rosin and a Diels-Alder Reagent to Yield a Non-Acid Functional Rosin Curing Agent 6.3 g maleic anhydride and 0.05 g phosphoric acid were added into the upper crude material (AAPD) at 150° C. The mixture was stirred at 180-190° C. for 4 hours under argon atmosphere. And then, the redundant maleic anhydride was removed by vacuum pump (3 mmHg) at 180° C. After being cooled down to room temperature, the material remained in the flask (Chemical 3 in Scheme 5, named AAPDMA) was ready to cure the epoxy.

Sample Preparation for Curing Study

To study the curing activity of methyl maleopimarate (MMAP), phenyl glycidyl ether (PGE) was used as the epoxide. In order to achieve a good mixing of the reactants, MMAP/PGE in molar ratio 1:2 together with the catalyst were first dissolved in $CHCl_3$, and then the solvent was removed in a vacuum at room temperature. To study the curing activity of abietyl glycidyl ether (AGLE), aniline was used as the curing agent. Similarly, an equivalent stoichiometric amount of AGLE and aniline (AGLE/aniline in molar ratio 2:1) together with a catalyst were first dissolved in ethyl ether, and then the solvent was removed in vacuum at room temperature. For both epoxy systems, 2-ethyl-4-methylimidazole was added as a catalyst during preparation at the level of 0.5 wt % of the total weight of epoxide and curing agent. The mixtures were sealed in glass vials and were kept in dry ice for a maximum of 48 h while waiting for curing tests.

Fabrication of Epoxy Membrane

In order to achieve a good mixture of the reactants, curing agent (AAPDMA), epoxy (DER 332E) and catalyst (2-ethyl-4-methylimidazole) were dissolved in small amount of acetone before it was stirred at room temperature for 30 min. Then the solvent was removed in vacuum oven, and the mixture was cured at fixed temperature. For example, 4.1 g AAPDMA, 1.9 g DER 332E and 0.06 g 2-ethyl-4-methylimidazole (1 wt % of the total weight of curing agent and epoxy) was dissolved in 10 ml acetone to make a homogeneous mixture under mechanical stir at room temperature. Then the solution was heated at 50° C. for 12 hours to remove the solvent in vacuum oven. After that, it was poured into a mould and cured at 100° C. for 2 hours and 160° C. for 2 hours. At last, a transparent, yellow membrane with the dimension of 100 mm×100 mm×0.5 mm was obtained. Before mechanical properties testing, the large membrane was cut into the dog-bone shape with dimension of 100 mm×20 mm×0.5 mm. All of the samples fabricated by this method were named "Epoxy 11", "Epoxy 12" and "Epoxy 25" respectively, based on the different ratio between AAPDMA and DER 332E used. The number following the word "Epoxy" represents the ratio of them. For example, "Epoxy 12" represents the sample, in which the ratio between acid value in AAPDMA and epoxy group in DER 332E was 2:1 used.

Curing Study by DSC and $^1H$ NMR

Nonisothermal curing of the epoxy systems was performed on a Mettler-Toledo 822e DSC in a nitrogen atmosphere. Heat scan ranging from −50 to 250° C. was performed at heating rates of 2.5, 5, 10, and 20° C./min, respectively. Approximate 5 mg of each of the above prepared samples was weighed and sealed in an aluminum DSC sample pan, and the curing was conducted immediately. The degree of conversion of the epoxy group at any instantaneous temperature (or time) during the curing reaction, α, was calculated from the area under the DSC exothermic peak:

$$\alpha = \frac{Q_t}{Q_{tot}}$$

where $Q_t$ was given by the fraction peak area at time t (or corresponding temperature T) and $Q_{tot}$ by the total peak area.

The cure reactions were studied by $^1$H NMR analysis of the reaction products. The reacted sample after curing on DSC and unreacted samples were examined using $^1$H NMR in CDCl$_3$.

Similar to the isothermal curing of many other epoxy systems, reaction was noted to take place during heating to the selected cure temperatures. Although approaches such as dropping the cold sample into a preheated DSC or curve fitting could be adopted to compensate the lost signal, in this embodiment the simple nonisothermal method was employed. It has been concluded that there is no fundamental contradiction between kinetic parameters determined from isothermal and nonisothermal experiments, though the inconsistency in Arrhenius parameters between these two methods persists. FIG. 3 shows the exothermic heat flows of nonisothermal curing of the model compounds in the DSC experiment. The DSC experiment results are summarized in Tables 1 and 2 of FIGS. 7 and 8. As the heating rate (β) increased, initial curing temperature ($T_i$), peak exothermic temperature ($T_p$) and temperature at curing end ($T_e$) all shifted to higher temperatures, and the range of curing temperature widened. However, the curing time actually decreased with heating rate increase. The enthalpy of cure reaction generally increased with heating rate up to 10° C./min, then showed a significant decrease at 20° C./min.

While the shift in the cure temperature of cure reaction with heating rate is more probably methodological, the dependence of cure reaction enthalpy on heating rate is supposed to have a chemical nature. Epoxy curing involves a sequence of elementary reactions; these elementary steps and reaction pathway are temperature dependent. The relatively low enthalpy at heating rate 20° C./min for both curing systems is likely related to the different reaction pathways involved at the higher cure temperature. DSC analysis measures the overall reaction enthalpy. Without a comprehensive analysis of the possible elementary reactions, DSC results can only provide very limited information on cure mechanism. Nevertheless, the dependence of cure kinetics on heating rate could be eliminated by extrapolating the results to infinitely slow heating rates (isothermal conditions), therefore "true" cure reaction temperature and Arrhenius parameters can be determined. The values of these curing reaction parameters at the zero heating rate were estimated from linear extrapolation and are also given in Tables 1 and 2, ranging from 119 to 149° C. for maleopimarate/EPP and from 124 to 175° C. for abietyl glycidyl ether/aniline, respectively. If the initial curing, peak and curing end temperatures at the zero heating rate can be used as references for the selection of temperatures in the isothermal curing study, then these temperatures fell within the conventional epoxy curing temperature range. By comparing the enthalpy of cure reaction on the basis of per mole of epoxide, it was interesting to note that the molar enthalpy of curing of abietyl glycidyl ether by aniline (~33 KJ/mol) was less than half of that of the curing of the phenyl glycidyl ether system. The latter showed a molar enthalpy of reaction (~91 KJ/mol) close to that of diglycidyl ether of bisphenol A cured with m-phenylene diamine. This result suggests that rosin-based epoxy tends to yield significantly lower enthalpy of reaction than the conventional epoxies.

FIG. 4 shows the progress of reaction conversion with curing temperature. The s-shaped curves of degree of conversion (α) versus temperature indicate that the cure reaction was autocatalytic. The slope reached a maximum in the range of low to medium conversions. This is a clear indication that the reaction intermediates accelerated the cure reaction. At higher conversions, the linearity is lost, indicating the decrease in reaction rate. Since there was no network structure formed in the model reaction systems, the slowdown of reaction in this region was probably due to the decrease in the reactant concentrations. FIG. 5 shows the cure rate as a function of curing temperature. It indicates that the maximum reaction rate occurred around the peak exothermic temperature, and increased with heating rate.

Activation energy was measured following the Kissinger's method:

$$E_a = -R\left[\frac{d\left(\ln\frac{\beta}{T_p^2}\right)}{d\left(\frac{1}{T_p}\right)}\right]$$

where β=heating rate; $T_p$=peak exothermic temperature (Kelvin); $E_a$=kinetic activation energy; and R=gas constant (1.987 cal/K-mol). The plot of $\ln(\beta/T_p^2)$ against $1/T_p$ fell in a good linear relationship (curves not shown), and the slope was equal to $-E_a/R$. The calculated value of $E_a$ was 65.3±4.8 KJ/mol for the methyl maleopimarate/1,2-epoxy-3-phenyl propane system and 91.6±5.2 KJ/mol for the abietyl glycidyl ether/aniline system, respectively.

The reactant mixture before curing and the product after curing were analyzed by $^1$H NMR. FIG. 4 shows $^1$H NMR spectra of the above two reaction systems before and after curing. The cured products in FIG. 6 were from the above nonisothermal DSC curing study at a heating rate at 2.5° C./min. The assignments of the chemical shifts correspond to those labels in FIG. 1. The chemical shifts of the oxirane in phenyl glycidyl ether at δ2.77, 2.91 and 3.36 (FIG. 8a) basically disappeared after cure reaction with methyl maleopimarate; instead, new peaks at δ3.65 and δ5.35, which were attributed to the methylene and methenyl groups connected with the newly formed ester and hydroxyl groups (FIG. 3a), respectively, were observed. The peaks at δ3.97 and δ4.16 were attributed to the diastereomeric protons of the methylene connecting with the oxirane, and disappeared after curing. Chemical shifts of the double bond (δ5.53), methyl group (δ3.67) of the rosin ester and other protons in the rosin moiety did not show any observable changes.

In the abietyl glycidyl ether/aniline reaction system (FIG. 8b), the peaks at δ2.57, 2.76 and 3.65, which were attributed to the oxirane, disappeared after reaction. A new peak at 3.40 attributed to the methylene group connected with aniline was noted. Similarly, the chemical shifts at δ5.71 and 5.32, which belonged to the two protons of the two double bonds in the rosin structure, and the chemical shifts of other protons in the rosin moiety did not change after curing.

Based on the $^1$H NMR results of cure reactions, the curing mechanisms for the two epoxy systems in this study can be suggested as in FIG. 1. In the presence of a base catalyst (2-ethyl-4-methyimidazole), rosin-based anhydride curing of epoxide selectively resulted in the formation of diester (FIG. 1a), and this result was consistent with the well established epoxy curing mechanisms using anhydride. Initially the catalyst activated the reaction by attacking the oxirane, forming a hydroxyl-containing intermediate (I). This intermediate reacted with the rosin-based anhydride to yield a monoester with a free carboxyl group, which then reacted with an epoxide to form a diester with a hydroxyl. The reaction continued in the same cycle. The cure reactions of rosin-based epoxy with aniline were also suggested as in FIG. 1b. According to Shechter et al. a primary and a secondary amine reacted with epoxide to give a secondary and a tertiary amine, respectively. There was no evidence of reaction (etherification) between epoxide and the newly formed hydroxyl groups noted. This was probably due to the equivalent stoichiometric amount of reactants used in the reaction system, where excess epoxide was not available for favorable etherification. In this embodiment, under the condition of 1:1 epoxy/anhydride (or 1:1 epoxy/amine) equivalent stoichiometry, the reaction selectively resulted in a hydroxyl ester or tertiary amine rather than polyether. In addition, according to Shechter et al., the esterification is the preferred reaction in a base-catalyzed system.

Rosin acid derivatives, glycidyl abietyl ether and methyl maleopimarate, were successfully synthesized as analogs for rosin-based epoxies and anhydride curing agents, respectively. The synthesis methods for the products and intermediates were examined in detail. The maleation of methyl abietate was relatively easy and gave a good yield, while the etherification of the abietic alcohol showed steric hindrance as reflected in the relatively low yield. The nonisothermal curing study by DSC suggested that both the curing reaction of epoxide with the rosin anhydride compound and the curing reaction of rosin epoxide with aniline were autocatalytic, and the cure reactions were similar to the respective conventional epoxy resin systems. In the presence of 2-methy-4-ethyl-imidazole catalyst and under the equivalent stoichiometric amount of epoxy and curing agent, the curing of rosin-based anhydride with 1,2-epoxy-3phenoxy-propoane selectively yielded a diester, and the curing of rosin-based epoxy cured with aniline selectively yielded a tertiary amine. There was no etherification noted in the cure reactions.

According to a further embodiment, in order to improve the flexibility of epoxy materials such as adhesives or coatings, gum rosin was employed as the raw material, followed by the esterification with polycaprolactone diol and reaction with maleic anhydride, to synthesize an epoxy curing agent. Its chemical structure was confirmed with the aid of $^1$H-NMR spectroscopy and Fourier transform infrared spectroscopy (FT-IR). After that, a serial of different epoxy compositions were fabricated by changing the weight ratio between curing agent and epoxy monomer based on their acid value and epoxy group value. Then the mechanical properties and thermal properties of them were investigated by universal mechanical testing machine and thermogravimetric analysis (TGA). The results indicate that the epoxy composition under the condition of 2:1 epoxy/anhydride equivalent stoichiometry has the best properties. These compositions can be used as new epoxy adhesives or coatings.

In one example, gum resin was employed as the raw material, followed by the esterification with polycaprolactone diol and reaction with maletic anhydride, to synthesize an epoxy curing agent (Scheme 5) at first, then a serial of epoxy membranes were fabricated and their mechanical and thermal properties were studied. The huge rosin maleopimaric acid anhydride groups were connected by long polycaprolactone diol, which might be more effective, compared with the reported flexibilizers, in decreasing the net-work density and then increasing the flexibility of epoxy matrix when it was used as epoxy curing agent.

In order to prove the chemical structure of AAPD and AAPDMA, the FT-IR and $^1$H-NMR spectra were employed. In FIG. 9, for the spectra of polycaprolactone diol, the broad stretching peak at 3490 cm$^{-1}$ is assigned to the hydroxyl group. But for AAPD and AAPDMA, this broad peak was disappeared and the other characteristic peak was remained. Compared with the line for AAPD, there are new signals appeared at 1862, 1783 cm$^{-1}$, which is the characteristic absorption peaks due to asymmetrical and symmetrical C=O stretching vibrations of anhydride group, which told us the maleic anhydride was introduced into AAPD successfully by Diels-Alder reaction.

FIGS. 10 and 11 are the $^1$H-NMR spectra for AAPD and AAPDMA respectively. The $^1$H-NMR signals in the range of δ 0 ppm to δ~3.5 ppm are assigned to the hydrogenated phenanthrene ring segments in AAPD and AAPDMA. They are complicated and not useful in determining the chemical structure of the final compounds so they do not appear in the figures. In FIG. 10, the chemical shifts at ~5.37 ppm and ~5.77 ppm were due to the alkene C—H, labeled as a and b in the structure respectively. The signals at ~3.62 ppm and ~4.27 ppm were assigned to the protons CH$_2$ (e) and CH$_2$ (d) in the glycol units. Compared with FIG. 12, in FIG. 11 the two peaks at ~5.37 ppm and ~5.77 ppm were combined into one characteristic peak, which was ascribed to the single alkene proton remaining in AAPDMA after reaction (proton f in FIG. 1). At the same time, a new signal at ~3.69 ppm was found, which can present the information of proton g.

In summary, the FT-IR and $^1$H-NMR information indicates that the designed compounds were synthesized successfully. As an epoxy curing agent, the acid value is an important factor, which can determine the weight ratio between epoxide and hardener before curing. To determine the acid values of the final products, a traditional and popular acid-base titration method was employed. After repeated three times for one sample, the acid value of AAPDMA was confirmed to be 81.9 mg KOH/g.

A dynamic differential scanning calorimetry scan is often used to monitor the curing behavior of epoxy resins. FIG. 12 shows the curing reaction of epoxy 11, epoxy 12 and epoxy 25 monitored by DSC respectively. Obviously, an exothermal peak associated with curing for each sample was observed in the diagram. But their peak exothermic temperature ($T_p$), the shape and number of peaks were different from each other.

For epoxy 11, there is only one exothermic peak during the heating. But for epoxy 12 and epoxy 25, two clear exothermic peaks appeared and these multiple exothermic peaks were similar with the former reports. It is well known that the reaction between epoxide and anhydride is very complex and a small change in the DSC curve can represent partial curing reaction of a certain segment in the system. In this example, because of the steric hindrance of the huge hydrogenated phenanthrene ring in the structure and the difficulties in mass transport results from the high viscosity of the system, the reactivity of the anhydride group in the hardener might be low. In theory, in the system of epoxy 11, the single peak in DSC curve was due to the primary anhydride-epoxy reaction leading a linear polymer only and maybe there were a lot of reagents remained unreacted. But for the system of epoxy 12 and epoxy 25, the epoxy is superfluous greatly and the anhydride group was "immerged" in the epoxy group, and this makes the reaction easier. So after the primary anhydride-epoxy reaction was finished, the residual epoxy group would react with the hydroxyl and carboxyl further and the crosslinked polymer was formed, which reflected multiple exothermic peak and different peak exothermic temperature in DSC diagram. In order to prove this hypothesis, the FT-IR spectra of cured epoxy resins were shown in FIG. 13. Obviously, for epoxy 11, there were characteristic absorption peaks at 1862 and 1783 cm$^{-1}$, which indicates that numerous anhydride groups remained unreacted in the system. For epoxy 12 and epoxy 25, these two peaks disappeared and the intension of C—O—C absorption band at 1040 cm$^{-1}$ was increased compared with that of epoxy 11, which means that significantly more ether group formed and no anhydride remained. In view of the different ratio between epoxide and anhydride, their curing behaviors and cured product are different from each other, although the reaction between epoxide and anhydride resulted in the ester primarily.

In epoxy 12 and epoxy 25, either the hydroxyl or carboxyl reacted with epoxy group will increase the net-work density of epoxy resin and decrease its flexibility and increase its tensile stress. FIG. 14 is the tensile stress-strain curves for epoxy 11, epoxy 12 and epoxy 25 respectively. Apparently, the typical curves for polymer were obtained. Their detailed values on tensile stress, tensile modulus and extension are listed in table I. The tensile stress of the epoxy resin increased quickly with the increase of ratio between epoxy group and acid value, from 5.5 MPa for epoxy 23 to 16.4 MPa for epoxy 25. The elongation at break decreased, from 15.8% for epoxy 23 to 5.1% for epoxy 25. It is well known that, epoxy adhesives do not often provide the degree of elongation or movement that is required for many applications. However, improved flexibility by adding chemical groups to epoxy structure will often result in the decreasing of other properties such as tensile stress and tensile modulus. Thus, an epoxy system with good integrated mechanical properties can be useful. In our experiment, epoxy 11 has an elongation of 15.2%, tensile stress of 12.9 MPa and tensile modulus of 611 MPa. These integrated properties might be due to the adding of the large and long chain hardener and the selected ratio between epoxy group and anhydride group.

TABLE I

Mechanical properties of different epoxy system

| Sample | Tensile stress (MPa) | Tensile Modulus (MPa) | Extension (%) |
| --- | --- | --- | --- |
| Epoxy 11 | 5.5 ± 1.1 | 242 ± 46 | 15.8 ± 1.8 |
| Epoxy 12 | 12.9 ± 0.8 | 611 ± 78 | 15.2 ± 2.6 |
| Epoxy 25 | 16.4 ± 1.0 | 634 ± 83 | 5.1 ± 1.4 |

Measurements

Acid value of AAPDMA was determined by acid-base titration method with 0.05 N NaOH/methanol. Phenolphthalein is indicator.

$^1$H-NMR spectra was recorded with a Bruker 300 MHz spectrometer at room temperature in deuterated chloroform (CDCl$_3$). Chemical shifts are reported relative to chloroform (δ 7.26) for $^1$H NMR. Fourier transform infrared spectra were recorded with NEXUS 670 FT-IR. The wavelength was from 4000 to 400 cm$^{-1}$ and the KBr pellet was used.

Differential scanning calorimetry (DSC) was conducted on a Mettler Toledo DSC 822e instrument. The specimens were sealed in 40 μL aluminum crucibles. All specimens were heated from 40 to 250° C. at 10° C./min. Each sample runs for three times. Nitrogen was used as a purge gas at a flow rate of 80 mL/min.

Thermogravimetric analysis (TGA) measurements were performed on a Rheometric Scientific STA Thermogravimetric Analyzer. Each sample was heated with a heating rate of 10° C./min in a nitrogen atmosphere up to 550° C. and tested twice.

Tensile test was performed on a screw-driven universal testing machine (Instron 4466) equipped with a 2 KN electronic load cell and mechanical grips. The tests were conducted at a crosshead speed of 5 mm/min. All the tensile samples were conditioned in 50% relative humidity (RH) and 23° C. for 4 days prior to tensile testing. All tests were carried out according to the ASTM standard, and five replicates were tested for each sample to obtain an average value.

In view of the many possible embodiments to which the principles of the disclosed methods, compositions and compounds may be applied, it should be recognized that the illustrated embodiments are only preferred examples and should not be taken as limiting the scope of the invention. Rather, the scope of the invention is defined by the following claims. We therefore claim as our invention all that comes within the scope and spirit of these claims.

What is claimed is:

1. An epoxide agent for an epoxy resin system, the epoxide agent comprising at least one non-acid functional rosin moiety and at least one epoxide moiety, wherein the epoxide agent has a structure represented by at least one of the following formulae:

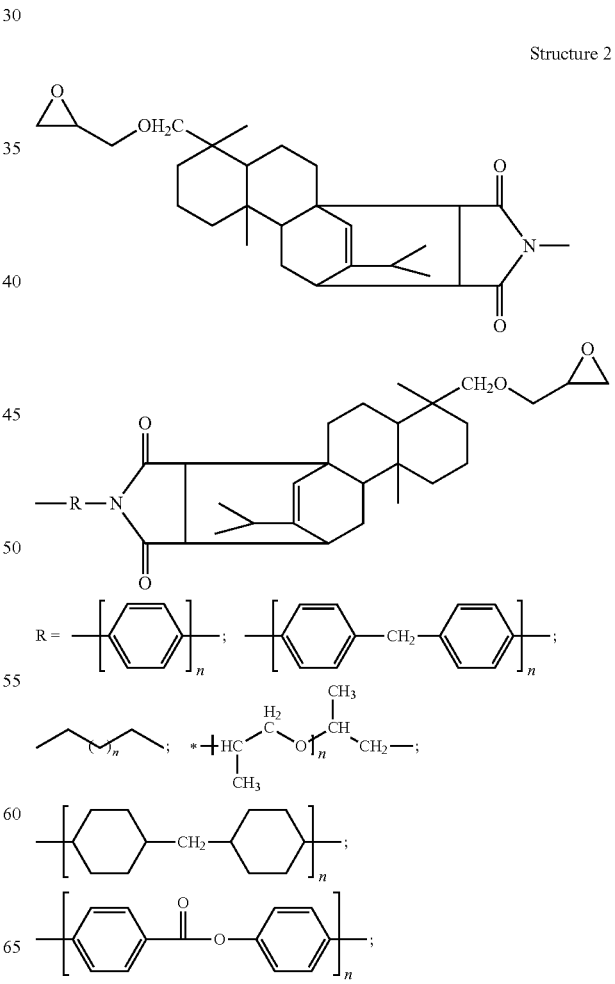

Structure 2

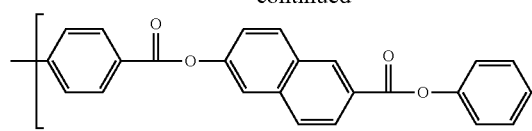
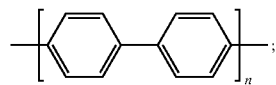
(n = 1-10);
Structure 3
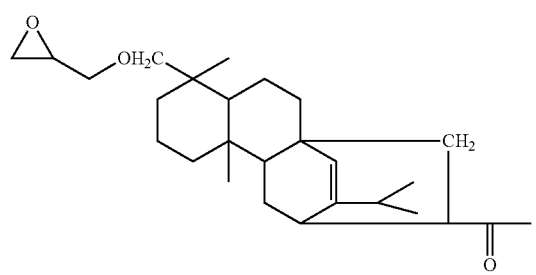
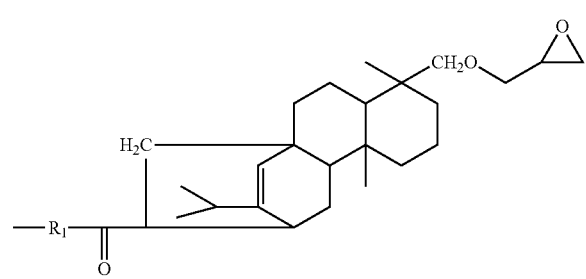
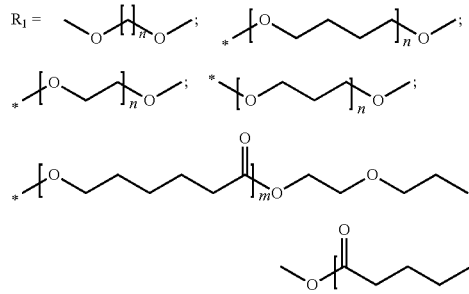
(n = 1-10)  (m = 1-10);
Structure 5
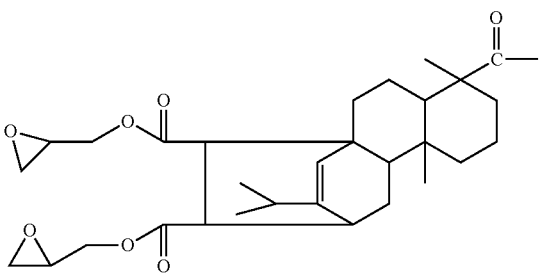
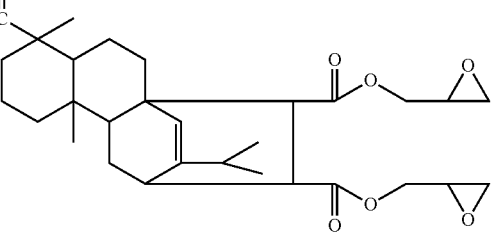
R = 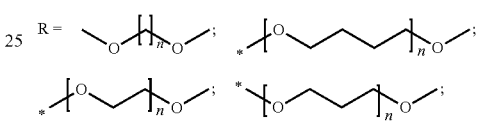
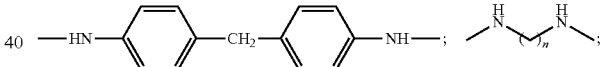
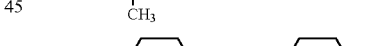
(n = 1-10)  (m = 1-10); or
Structure 10
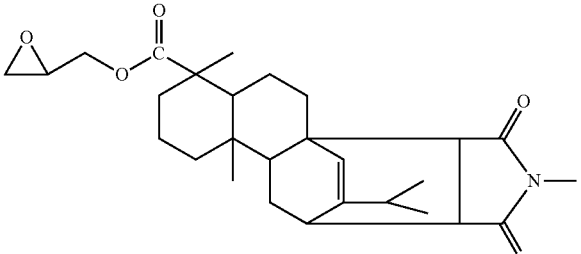
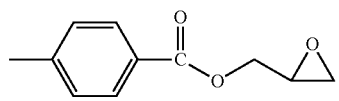

Structure 11
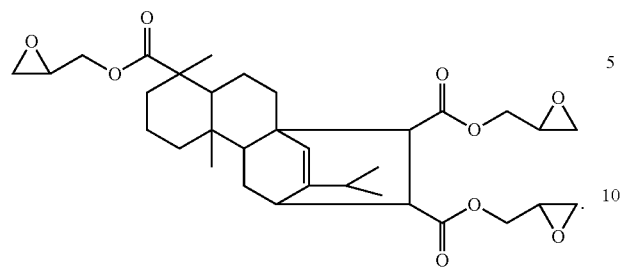
* * * * *